United States Patent
Satake

(10) Patent No.: US 10,923,220 B2
(45) Date of Patent: Feb. 16, 2021

(54) PROGRAM, DEVICE, SYSTEM AND METHOD FOR PATIENT WHO IS ATTEMPTING TO QUIT SMOKING

(71) Applicant: CUREAPP, INC., Tokyo (JP)

(72) Inventor: Kohta Satake, Tokyo (JP)

(73) Assignee: CUREAPP, INC., Tokyo (JP)

(*) Notice: Subject to any disclaimer, the term of this patent is extended or adjusted under 35 U.S.C. 154(b) by 450 days.

(21) Appl. No.: 15/580,291

(22) PCT Filed: Apr. 20, 2017

(86) PCT No.: PCT/JP2017/015927
§ 371 (c)(1),
(2) Date: Dec. 7, 2017

(87) PCT Pub. No.: WO2018/193592
PCT Pub. Date: Oct. 25, 2018

(65) Prior Publication Data
US 2019/0221297 A1    Jul. 18, 2019

(51) Int. Cl.
G16H 20/10    (2018.01)
A61B 5/08    (2006.01)
G16H 10/00    (2018.01)

(52) U.S. Cl.
CPC .......... *G16H 20/10* (2018.01); *A61B 5/082* (2013.01); *G16H 10/00* (2018.01)

(58) Field of Classification Search
CPC ........ A61B 5/082; G16H 10/00; G16H 20/00; G16H 20/10
See application file for complete search history.

(56) References Cited

U.S. PATENT DOCUMENTS

2008/0126277 A1* 5/2008 Williams ............ G06F 19/3481
706/14
2013/0102003 A1 4/2013 Gibbs
(Continued)

FOREIGN PATENT DOCUMENTS

JP    2005-070953 A    3/2005
JP    2005-181101 A    7/2005
(Continued)

OTHER PUBLICATIONS

International Search Report issued in corresponding application No. PCT/JP2017/015927 dated Jun. 20, 2017 (5 pages).
(Continued)

*Primary Examiner* — Jerry-Daryl Fletcher
(74) *Attorney, Agent, or Firm* — Osha Bergman Watanabe & Burton

(57) ABSTRACT

A non-transitory computer-readable medium stores a program designed to be used for a patient attempting to quit smoking. The program causes a computer to execute: receiving report information input by the patient and indicative of the presence or absence of smoking by the patient; receiving a biomarker concentration measurement value measured from a biological sample of the patient by a biomarker concentration meter for measuring a biomarker concentration indicative of a smoking state; based on the received biomarker concentration measurement value and a biomarker concentration reference value, determining consistency between the biomarker concentration measurement value and the report information; based on a result of the consistency determination, generating smoking cessation therapy information for smoking cessation therapy to be performed for the patient; and transmitting the generated smoking cessation therapy information to a patient-side device.

10 Claims, 14 Drawing Sheets

(56) References Cited

U.S. PATENT DOCUMENTS

2014/0378790 A1* 12/2014 Cohen .................... A61B 5/082
                                                                600/309
2015/0065825 A1*  3/2015 Utley ................. A61B 5/14551
                                                                600/322

FOREIGN PATENT DOCUMENTS

| JP | 2014-531031 A | 11/2014 |
| JP | 2017-045254 A |  3/2017 |
| WO | 2016/178276 A1 | 11/2016 |

OTHER PUBLICATIONS

Written Opinion of the International Searching Authority issued in corresponding application No. PCT/JP2017/015927 dated Jun. 20, 2017 (4 pages).

* cited by examiner

PROGRAM, DEVICE, SYSTEM AND METHOD FOR PATIENT WHO IS ATTEMPTING TO QUIT SMOKING

BACKGROUND

Technical Field

The present invention relates to a program, a device, a system and a method for a patient who is attempting to quit smoking.

Description of the Related Art

It is not always easy for a person who has continued to smoke to kick the smoking habit. A nicotine-dependent state caused by continuous (habitual) smoking is classified into two states: physical dependence; and psychological dependence. Generally, for the physical nicotine dependence, drug or pharmacological therapy using a smoking-cessation aid such as varenicline or nicotine preparation is performed, and, for the psychological nicotine dependence, behavioral therapy, cognitive-behavioral therapy and coaching by a health professional are performed. The behavioral therapy means a therapeutic procedure in which a health professional prompts a patient to practice a behavior (therapeutic behavior) which is expected to produce a therapeutic effect when implemented. Among various types of behavioral therapies, a therapeutic procedure in which, when a smoking urge, i.e., an urge to smoke, occurs, a certain action other than a smoking action is performed to thereby avoid a smoking action, is referred to as "substitute behavioral therapy". The cognitive-behavioral therapy means a therapeutic procedure in which a gap between patient's understanding (cognition) and a fact from a scientific standpoint (a gap in cognition) is corrected to thereby make a patient's behavioral change. The coaching means providing to a patient knowledge pertaining to diseases to thereby educate, encourage or praise the patient.

In the following Prior Art Document 1, there is proposed a system for providing smoking cessation therapy, based on conditions and/or a smoking cessation therapy history self-reported by a patient during smoking cessation therapy.

CITATION LIST

Patent Document

Patent Document WO 2016/178276A

As to a result of therapy using varenicline, although a 3-month smoking cessation success rate is about 65%, many persons will restart smoking, and consequently a one-year smoking cessation success rate will be only about 35%. Persons who successfully stop smoking once by pharmacological therapy will restart smoking at a high rate. This is probably because psychological dependence has not been resolved. Psychological dependence is a mental disorder, and requires daily detailed supports by a health professional or the like. However, a health professional can be involved only at each outpatient visit. There are often the cases where the total number, frequency, period, etc., of outpatient services which can be taken within health-care services covered by health insurance are limited. For example, in Japan, the number of outpatient services which can be taken within health-care services covered by health insurance is only five, and the frequency of the outpatient services is about one time two weeks to one month. Thus, the entire therapy will be terminated within about three months. Moreover, outpatient service hours are also limited, so that it is often the case that, even when a patient who is attempting to quit smoking (patient during smoking cessation therapy) decides to consult a medical doctor, it is necessary to take long time until he/she sees a medical doctor, because he/she has to go to a hospital. After the outpatient service hours, it is impossible to consult a medical doctor in the first place. As above, a time usable for smoking cessation coaching by a health professional is extremely limited, and a patient with nicotine dependence cannot consult a health professional when he/she wishes to do so, and it is difficult to receive smoking cessation therapy over a long period of time.

In smoking cessation therapy, it is important to timely provide appropriate therapy to a patient who has restarted smoking despite being under smoking cessation therapy. It is possible that a medical doctor provides smoking cessation therapy after checking whether or not an outpatient has restarted smoking, by subjecting the outpatient to measurement of a carbon monoxide (CO) concentration or the like contained in his/her exhaled breath. However, even in the case where the outpatient smoked once, after a certain period of time has elapsed since the smoking, the CO concentration contained in the exhaled breath decreases and therefore it becomes impossible to check whether or not the outpatient has smoked. The total number, frequency, period, etc., of outpatient services are limited, as mentioned above. Thus, an extended period of time from smoking to the next outpatient service makes it impossible to detect the fact that the outpatient smoked, and thus provide appropriate therapy. If the outpatient restarts smoking and returns to habitual smoking before the next outpatient service, it becomes extremely difficult to promote the smoking cessation therapy. There might be a possibility that the outpatient does not return for follow-up visit.

The Prior Art Document 1 discloses a system for providing smoking cessation therapy, based on conditions and/or a smoking cessation therapy history self-reported by a patient during smoking cessation therapy. However, the system disclosed in the Prior Art Document 1 is based on a self-report by a patient during smoking cessation therapy, and thus the self-reported information is not necessarily accurate. Particularly, when a patient smoked despite being under smoking cessation therapy, there is a possibility that the patient makes a false report that he/she has not smoked since start of the therapy, i.e., continues to quit smoking. In this case, despite the fact that the patient has restarted smoking, the patient will receive a therapy for a patient who continues to quit smoking. Thus, appropriate therapy is not necessarily provided.

SUMMARY

One or more embodiments of the present invention provide a program, a device, a system and a method for a patient who is attempting to quit smoking, which is designed to determine consistency between a smoking report and a biomarker concentration measurement value and provide appropriate smoking cessation therapy based on a result of the determination.

Technical Advantages

One or more embodiments of the present invention can provide one or more of the following technical advantages that, when executed by a computer or computer system, improve the functionality of the computer system over conventional technology. According to one or more embodiments of the present invention, there is provided a non-transitory computer-readable medium storing a program designed to be used for a patient who is attempting to quit smoking. The program causes a computer to execute: a step of receiving report information input by the patient and indicative of the presence or absence of smoking by the patient; a step of receiving a biomarker concentration measurement value measured from a biological sample of the patient by a biomarker concentration meter for measuring a biomarker concentration indicative of a smoking state; a consistency determination step of, based on the received report information, the received biomarker concentration measurement value and a biomarker concentration reference value, determining consistency between the biomarker concentration measurement value and the report information; a step of, based on a result of the consistency determination, generating smoking cessation therapy information for smoking cessation therapy to be performed for the patient; and a step of transmitting the generated smoking cessation therapy information to a patient-side device.

The program according to one or more embodiments of the present invention may be configured to cause the computer to further execute a step of receiving a time stamp indicative of a clock time of the measurement of the biomarker concentration measurement value, wherein the measurement clock time may be determined by the biomarker concentration meter or by a device for transmitting the biomarker concentration measurement value.

In the program according to one or more embodiments of the present invention, the report information indicative of the presence or absence of smoking by the patient may include the number of cigarettes smoked and a smoking timing, wherein the consistency determination step may include the substeps of: based on the number of cigarettes smoked, the smoking timing and an attenuation function of the biomarker concentration, setting an upper limit value of the biomarker concentration, as the biomarker concentration reference value; comparing the biomarker concentration measurement value with the upper limit value of the biomarker concentration; and, when the biomarker concentration measurement value is greater than the upper limit value of the biomarker concentration, determining that the report information and the biomarker concentration measurement value are inconsistent with each other.

In the above program, the consistency determination step may further include the substeps of: based on the number of cigarettes smoked, the smoking timing and the attenuation function of the biomarker concentration, setting a lower limit value of the biomarker concentration, as the biomarker concentration reference value; comparing the biomarker concentration measurement value with the lower limit value of the biomarker concentration; when the biomarker concentration measurement value is greater than the upper limit value of the biomarker concentration, determining that the biomarker concentration measurement value and the report information are inconsistent with each other, due to underreporting; and, when the biomarker concentration measurement value is equal to or greater than the lower limit value of the biomarker concentration, determining that the biomarker concentration measurement value and the report information are inconsistent with each other, due to overreporting.

According to one or more embodiments of the present invention, there is provided a program designed to be used for a patient who is attempting to quit smoking. The program is configured to cause a computer to execute the steps: acquiring a biomarker concentration measurement value measured from a biological sample of the patient by a biomarker concentration meter for measuring a biomarker concentration indicative of a smoking state; accepting an input of report information by the patient, wherein the report information is indicative of the presence or absence of smoking by the patient; transmitting the report information and the biomarker concentration measurement value to a server so as to set smoking cessation therapy information; receiving the smoking cessation therapy information from the server; and, based on the smoking cessation therapy information received from the server, presenting information for smoking cessation therapy, to the patient.

The program according to one or more embodiments of the present invention may be configured to cause a computer to execute, as a substitute for the step of transmitting the report information and the biomarker concentration measurement value to a server: a consistency determination step of, based on the acquired biomarker concentration measurement value and a biomarker concentration reference value, determining consistency between the biomarker concentration measurement value and the report information, so as to set smoking cessation therapy information; and a step of transmitting a result of the consistency determination to the server.

In the program according to one or more embodiments of the present invention, the biological sample may be exhaled breath, wherein the biomarker may be carbon monoxide (CO), and the biomarker concentration meter may be a CO concentration meter.

Alternatively, the biological sample may be saliva, wherein the biomarker may be nicotine, and the biomarker concentration meter may be a nicotine concentration meter.

According to one or more embodiments of the present invention, there is provided a set of programs designed to be used for a patient who is attempting to quit smoking. The set of programs is configured to cause a computer to execute: a step of accepting an input of report information by the patient, wherein the report information is indicative of the presence or absence of smoking by the patient; a step of measuring a biomarker concentration indicative of a smoking state, from a biological sample of the patient; a consistency determination step of, based on the biomarker concentration measurement value and a biomarker concentration reference value, determining consistency between the biomarker concentration measurement value and the report information; a step of, based on a result of the consistency determination, generating smoking cessation therapy information indicative of smoking cessation therapy to be performed for the patient; and a step of, based on the smoking cessation therapy information, presenting information for the smoking cessation therapy, to the patient. The term "a set of programs" herein may be a set of multiple programs or may be single program.

According to one or more embodiments of the present invention, there is provided a server designed to be used for a patient who is attempting to quit smoking. The server comprises a control section and a communication section, wherein the control section is operable to: receive, via the communication section, report information input by the patient and indicative of the presence or absence of smoking by the patient; receive, via the communication section, a biomarker concentration measurement value measured from a biological sample of the patient by a biomarker concentration meter for measuring a biomarker concentration indicative of a smoking state; based on the received biomarker concentration measurement value and a biomarker concentration reference value, determine consistency between the biomarker concentration measurement value and the report information; based on a result of the consistency determination, generate smoking cessation therapy information for smoking cessation therapy to be performed for the patient; and transmit the generated smoking cessation therapy information via the communication section.

According to one or more embodiments of the present invention, there is provided a patient-side device designed to be used for a patient who is attempting to quit smoking. The patient-side device comprises a control section, an input acceptance section, an output section and a communication section, wherein the control section is operable to: acquiring a biomarker concentration measurement value measured from a biological sample of the patient by a biomarker concentration meter for measuring a biomarker concentration indicative of a smoking state; accepting an input of report information by the patient via the input acceptance section, wherein the report information is indicative of the presence or absence of smoking by the patient; transmitting, via the communication section, the report information and the biomarker concentration measurement value to a server so as to set smoking cessation therapy information; receiving the smoking cessation therapy information from the server via the communication section; and, based on the smoking cessation therapy information received from the server, presenting information for smoking cessation therapy, to the patient via the output section.

According to one or more embodiments of the present invention, there is provided a system comprising one or more computers designed to be used for a patient who is attempting to quit smoking. The one or more computers are configured to: accept an input of report information by the patient, wherein the report information is indicative of the presence or absence of smoking by the patient; measure a biomarker concentration indicative of a smoking state, from a biological sample of the patient; based on the biomarker concentration measurement value and a biomarker concentration reference value, determine consistency between the biomarker concentration measurement value and the report information; based on a result of the consistency determination, generate smoking cessation therapy information indicative of smoking cessation therapy to be performed for the patient; and, based on the smoking cessation therapy information, present information for the smoking cessation therapy, to the patient.

According to one or more embodiments of the present invention, there is provided a method configured to be performed with one or more computers designed to be used for a patient who is attempting to quit smoking. The method comprises: a step of accepting an input of report information by the patient, wherein the report information is indicative of the presence or absence of smoking by the patient; a step of measuring a biomarker concentration indicative of a smoking state, from a biological sample of the patient; an inconsistency determination step of, based on the biomarker concentration measurement value and a biomarker concentration reference value, determining consistency between the biomarker concentration measurement value and the report information; a step of, based on a result of the consistency determination, generating smoking cessation therapy information indicative of smoking cessation therapy to be performed for the patient; and a step of, based on the smoking cessation therapy information, presenting information for the smoking cessation therapy, to the patient.

One or more embodiments of the present invention provide an improvement over existing computer-implemented technologies by making it possible to determine consistency between the report information indicative of the presence or absence of smoking by the patient (indicative of whether or not the patient has smoked), and the biomarker concentration measurement value of the patient, to thereby determine whether or not the patient's report is false, and then implement appropriate smoking cessation therapy based on a result of the determination. In one or more embodiments of the present invention, the report information indicative of the presence or absence of smoking by the patient includes the number of cigarettes smoked and the smoking timing. In this case, the determination as to whether or not the report is false can also be made in terms of the number of cigarettes smoked and the smoking timing, so that it becomes possible to more carefully provide smoking cessation therapy based on a result of the determination.

By employing the features of the embodiments of the present invention, it becomes possible to implement required therapy timely when necessary. For example, it becomes possible to provide appropriate smoking cessation therapy to a patient who has restarted smoking, before he/she returns to habitual smoking. By using an electronic device such as a smartphone, a patient can receive smoking cessation therapy always and for a long period of time via the electronic device. This makes it possible to effectively perform therapy for a patient who is attempting to quit smoking, particularly, who psychologically depends on smoking.

DETAILED DESCRIPTION OF EMBODIMENTS

Figure 1:
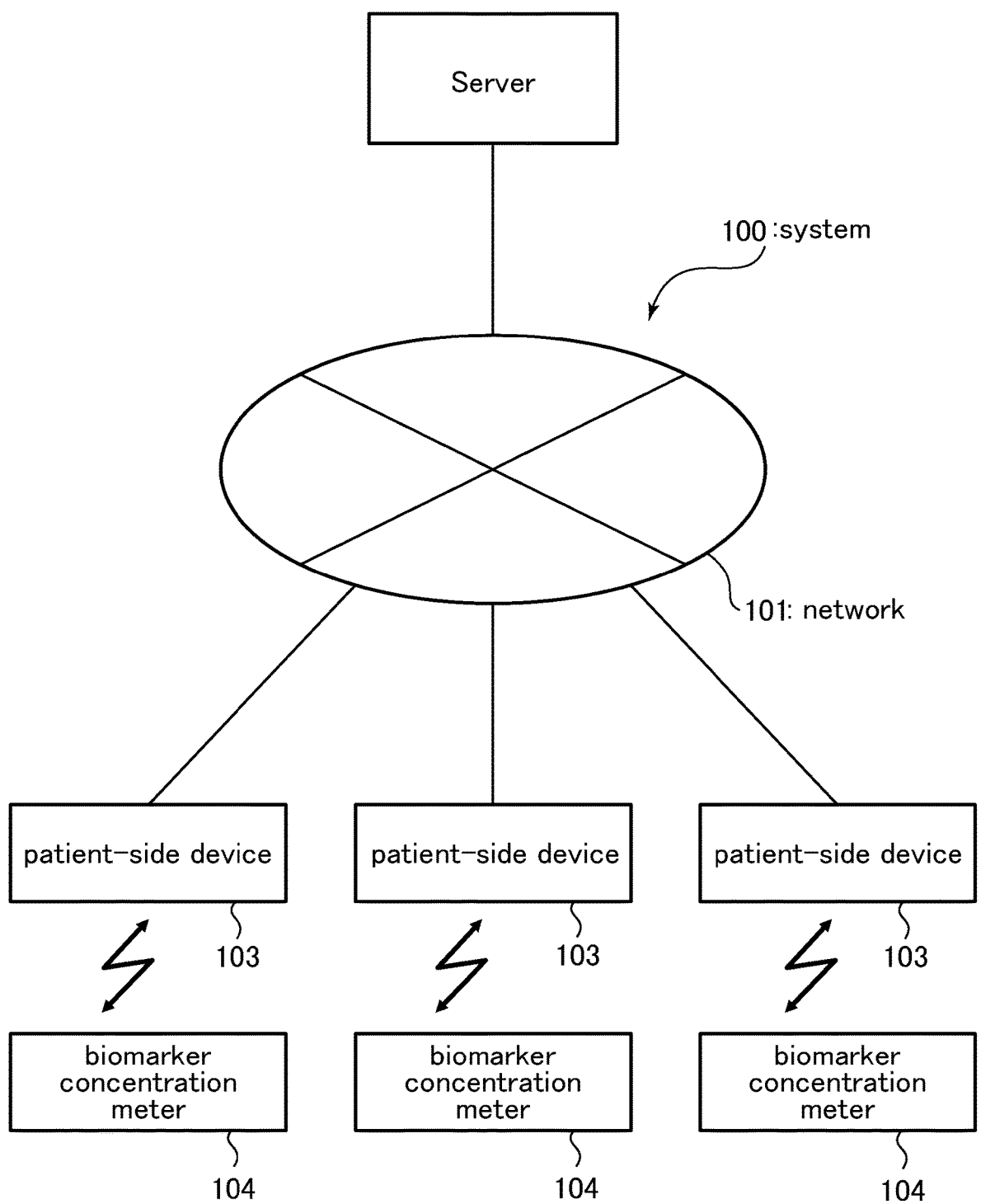
FIG. 1 is a block diagram depicting a configuration of a system according to one or more embodiments of the present invention.

FIG. 1 depicts a configuration of a system according to one or more embodiments of the present invention. This system 100 is designed to be used for a patient who is attempting to quit smoking (patient during smoking cessation therapy), and comprises: a server 102; at least one patient-side device 103 which is an electronic device used by the patient; and a biomarker concentration meter 104 to be used by the patient. In one or more embodiments, the server 102 and the patient-side device 103 are connected to each other via a network 101. Further, the patient-side device 103 and the biomarker concentration meter 104 are connected to each other in a wired or wireless manner. Alternatively, the biomarker concentration meter 104 may be connected to the network 101 the patient-side device 103 without going through the patient-side device 103.

Figure 2:
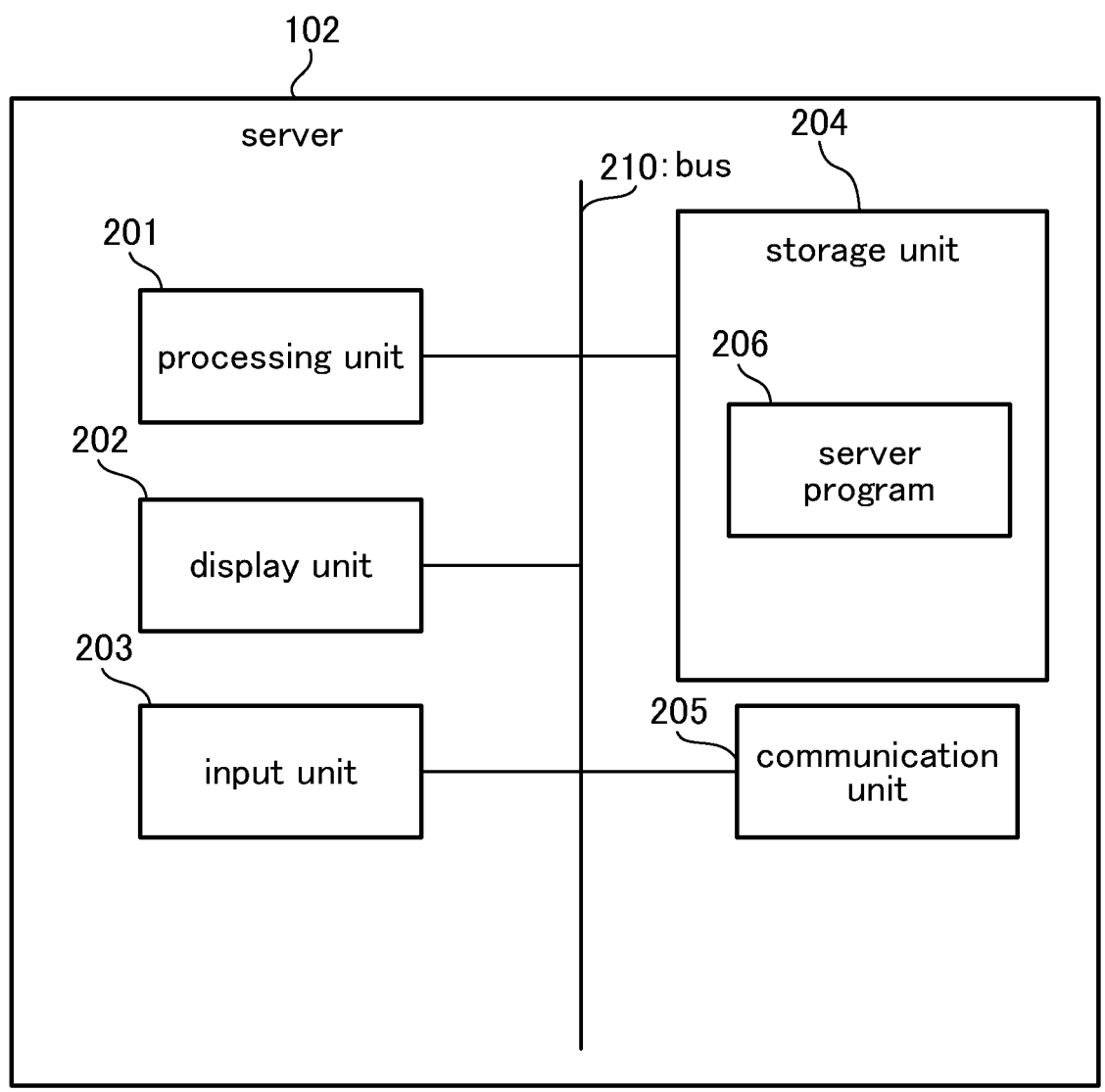
FIG. 2 is a block diagram depicting a hardware configuration of a server in the system according to one or more embodiments.

FIG. 2 depicts a hardware configuration of the server 102. The server 102 is a computer comprising a processing unit 201, a display unit 202, an input unit 203, a storage unit 204, and a communication unit 205. In one or more embodiments, these units are connected to each other via a bus 210. Alternatively, the server may be configured such that the units are connected to each other individually as needed basis. The display unit 202 has a function of displaying information to a user. The input unit 203 has a function of accepting an input from a user, like a keyboard, a mouse or the like. The storage unit 204 stores therein a server program 206. The storage unit 204 may be any type of storage unit, such as a non-volatile memory or a volatile memory, as long as it is capable of storing information therein. The communication unit 205 is configured to perform wire communication using an Ethernet (trademark) cable or the like, or wireless communication using cellular network, wireless LAN or the like, to establish connection to the network 101.

Figure 3:
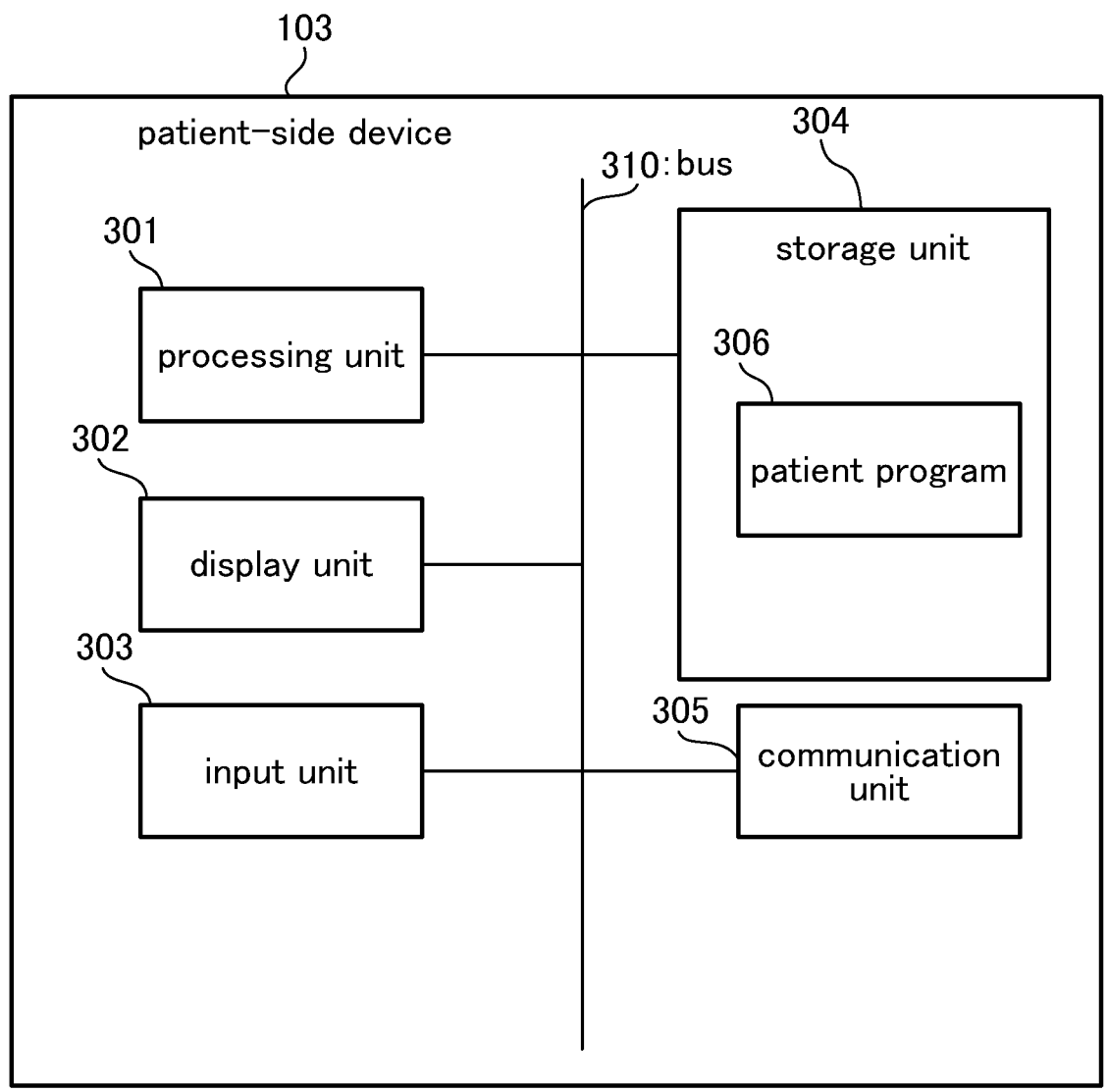
FIG. 3 is a block diagram depicting a hardware configuration of a patient-side device in the system according to one or more embodiments.

FIG. 3 is a block diagram depicting a hardware configuration of the patient-side device 103 which is an electronic device used by the patient. As used herein, the term "patient" means a person who is attempting to quit smoking through the use of the embodiments of the present invention, but does not necessarily mean a person who is undergoing smoking cessation therapy under coaching by a health professional. The patient-side device 103 comprises a processing unit 301, a display unit 302, an input unit 303, a storage unit 304, and a communication unit 305. In one or more embodiments, these units are connected to each other via a bus 310. Alternatively, the patient-side device may be configured such that the units are connected to each other individually as needed basis. The patient-side device 303 may be composed of a desktop computer or a notebook computer, or may be a personal digital assistance, a mobile phone, a smartphone or a tablet terminal. The display unit 302 has a function of displaying information to a user. The input unit 303 has a function of accepting an input from a user, like a keyboard, a mouse or the like. When the patient-side device 103 is composed of a smart phone or a tablet terminal, the display unit 302 and the input unit 303 may be integrated together as a touch panel. The storage unit 304 stores therein a patient program 306 for the patient-side device. The storage unit 304 may be any type of storage unit, such as a non-volatile memory or a volatile memory, as long as it is capable of storing information therein. The communication unit 305 is configured to perform wire communication using an Ethernet (trademark) cable or the like, or wireless communication using cellular network, Bluetooth (trademark) connection, wireless LAN or the like, to establish connection to the network 101 and the biomarker concentration meter 104.

Figure 4:
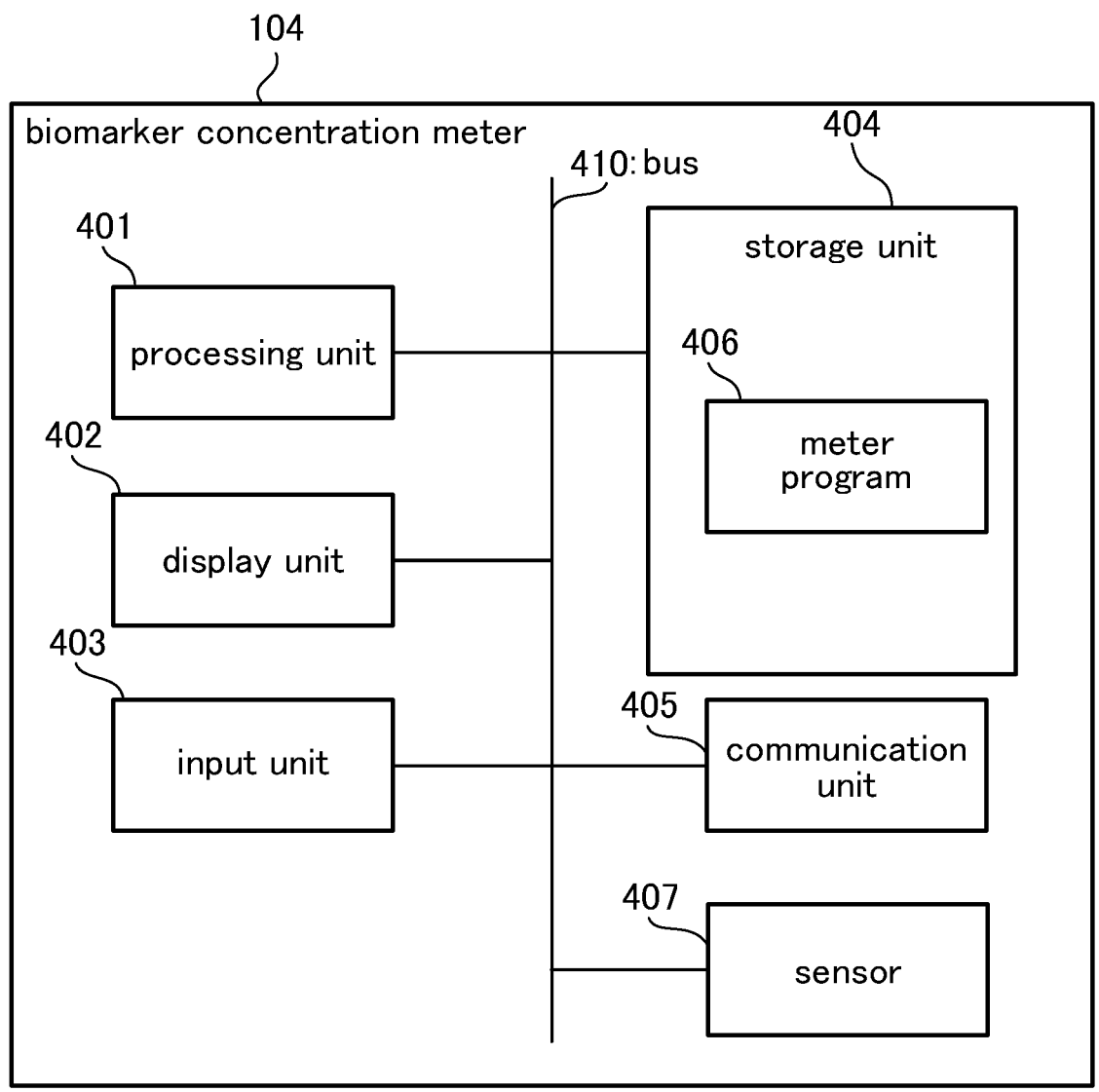
FIG. 4 is a block diagram depicting a hardware configuration of a biomarker concentration meter in the system according to one or more embodiments.

FIG. 4 is a block diagram depicting a hardware configuration of the biomarker concentration meter 104 used by the patient. The biomarker concentration meter 104 comprises a processing unit 401, a display unit 402, an input unit 403, a storage unit 404, a communication unit 405, and a sensor 407. In one or more embodiments, these units are connected to each other via a bus 410. Alternatively, the biomarker concentration meter may be configured such that the units are connected to each other individually as needed basis. The display unit 402 has a function of displaying information to a user. The input unit 403 has a function of accepting an input from a user, like a push-button or the like. The display unit 402 and the input unit 403 may be integrated together as a touch panel. The storage unit 404 stores therein a meter program 406 for the biomarker concentration meter 104. The storage unit 404 may be any type of storage unit, such as a non-volatile memory or a volatile memory, as long as it is capable of storing information therein. The communication unit 405 is configured to perform wire communication using an Ethernet (trademark) cable or the like, or wireless communication using cellular network, wireless LAN, Bluetooth (trademark) connection or the like, to establish connection to the patient-side device 103. The sensor 407 is configured to detect a biomarker from a biological sample of the patient and measure and output the concentration of the biomarker. The sensor is also configured to transmit the output to another device via the communication unit 405 and display the output on the display unit 402.

Figure 5:
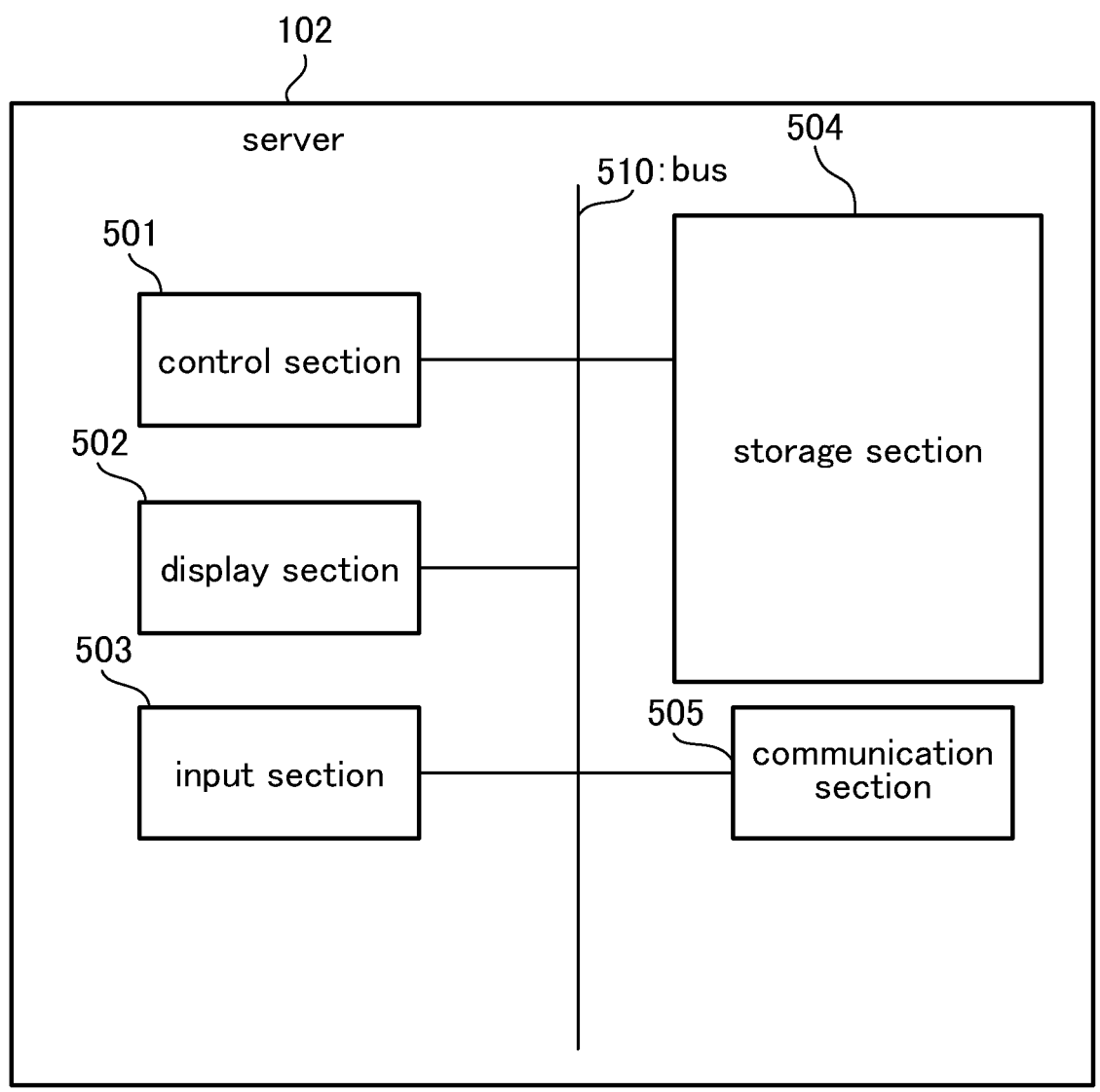
FIG. 5 is a block diagram depicting a functional configuration of the server in the system according to one or more embodiments.
Figure 6:
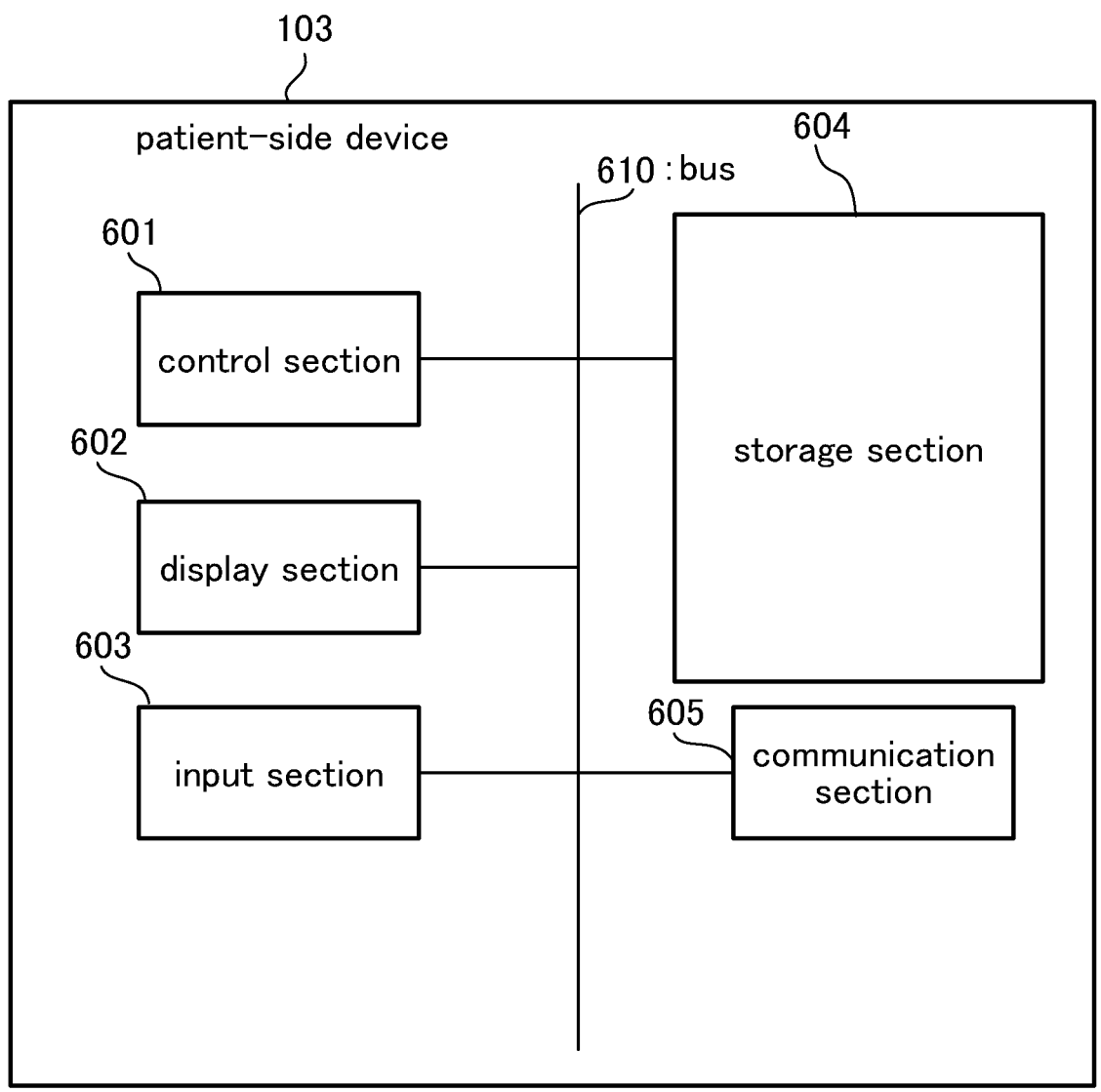
FIG. 6 is a block diagram depicting a functional configuration of the patient-side device in the system according to one or more embodiments.
Figure 7:
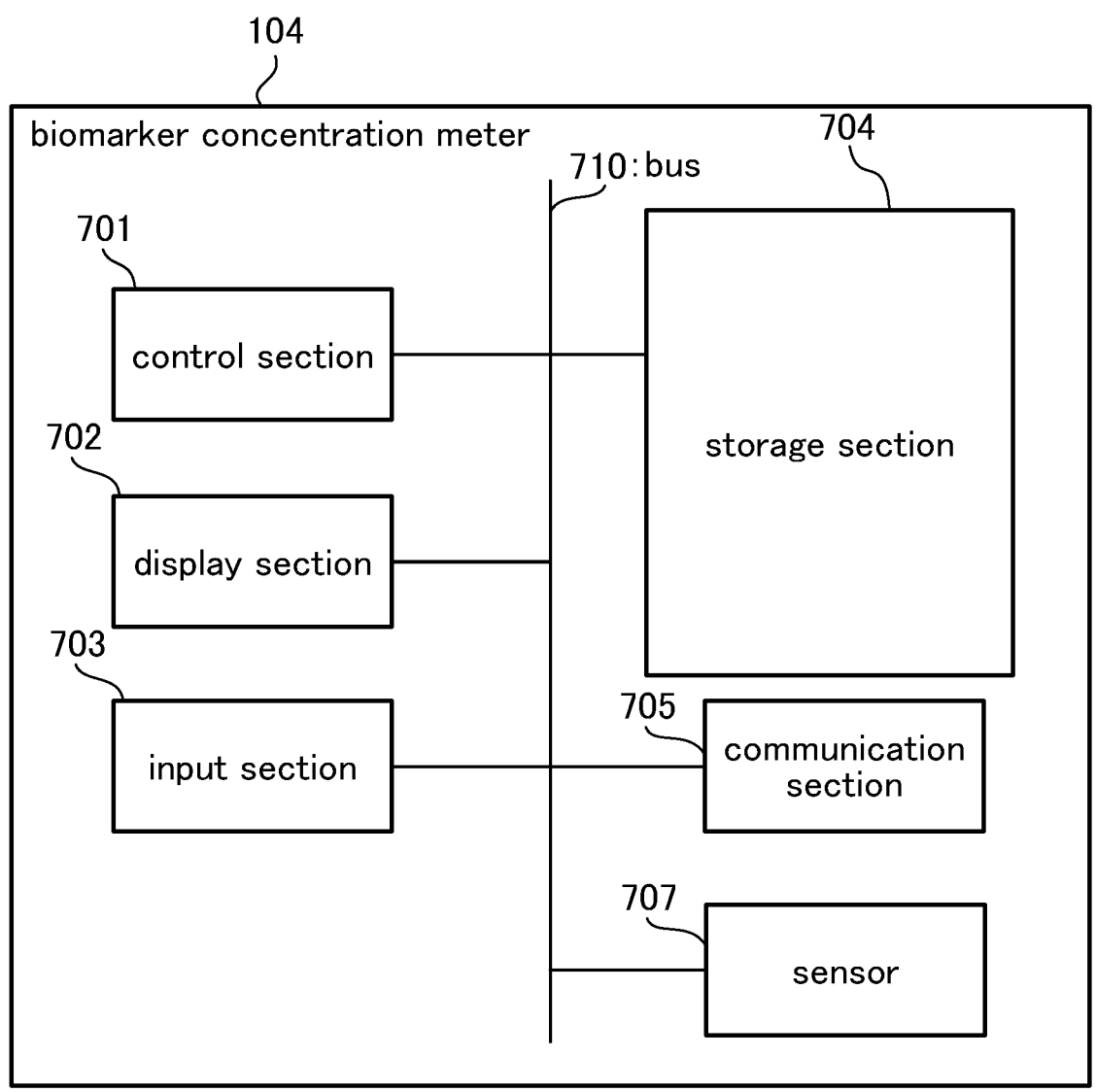
FIG. 7 is a block diagram depicting a functional configuration of the biomarker concentration meter in the system according to one or more embodiments.

FIGS. 5 to 7 depict, respectively, examples of functional configurations of the server 102, the patient-side device 103, and the biomarker concentration meter 104. The server 102 comprises a control section 501, a display section 502, an input section 503, a storage section 504 and a communication section 505, and the patient-side device 103 comprises a control section 601, a display section 602, an input section 603, a storage section 604 and a communication section 605. Further, the biomarker concentration meter 104 comprises a control section 701, a display section 702, an input section 703, a storage section 704, a communication section 705, and a sensor 707. Each of the control sections operates to execute control such as information processing. Each of the display sections operates to display information in such a manner as to enable a user to visibly recognize the information. Each of the input sections operates to accept an input from a user. Each of the storage sections operates to store therein data or the like. Each of the communication sections operates to transmit and receive information with respect to other devices. The sensor 707 operates to detect a biomarker from a biological sample of the patient and measure and output the concentration of the biomarker. In one or more embodiments, the above functional sections are realized by executing the programs in the hardware such as the processing units described in FIGS. 2 to 4. Alternatively, these functional sections may be realized based on hardware by providing an electronic circuit or the like capable of realizing the functional sections.

First Embodiment

An operation of a system according to a first embodiment of the present invention will be described. In the first embodiment, a smartphone is used as the patient-side device 103, and a carbon monoxide concentration meter (CO monitor) is used as the biomarker concentration meter 104. In the following embodiments, for the sake of explanation, the operation will be described on an assumption that the system comprises one patient-side device 103 and one CO monitor 104. However, it is to be understood that the system may comprise two or more patient-side devices 103 and two or more CO monitors 104.

Figure 8:
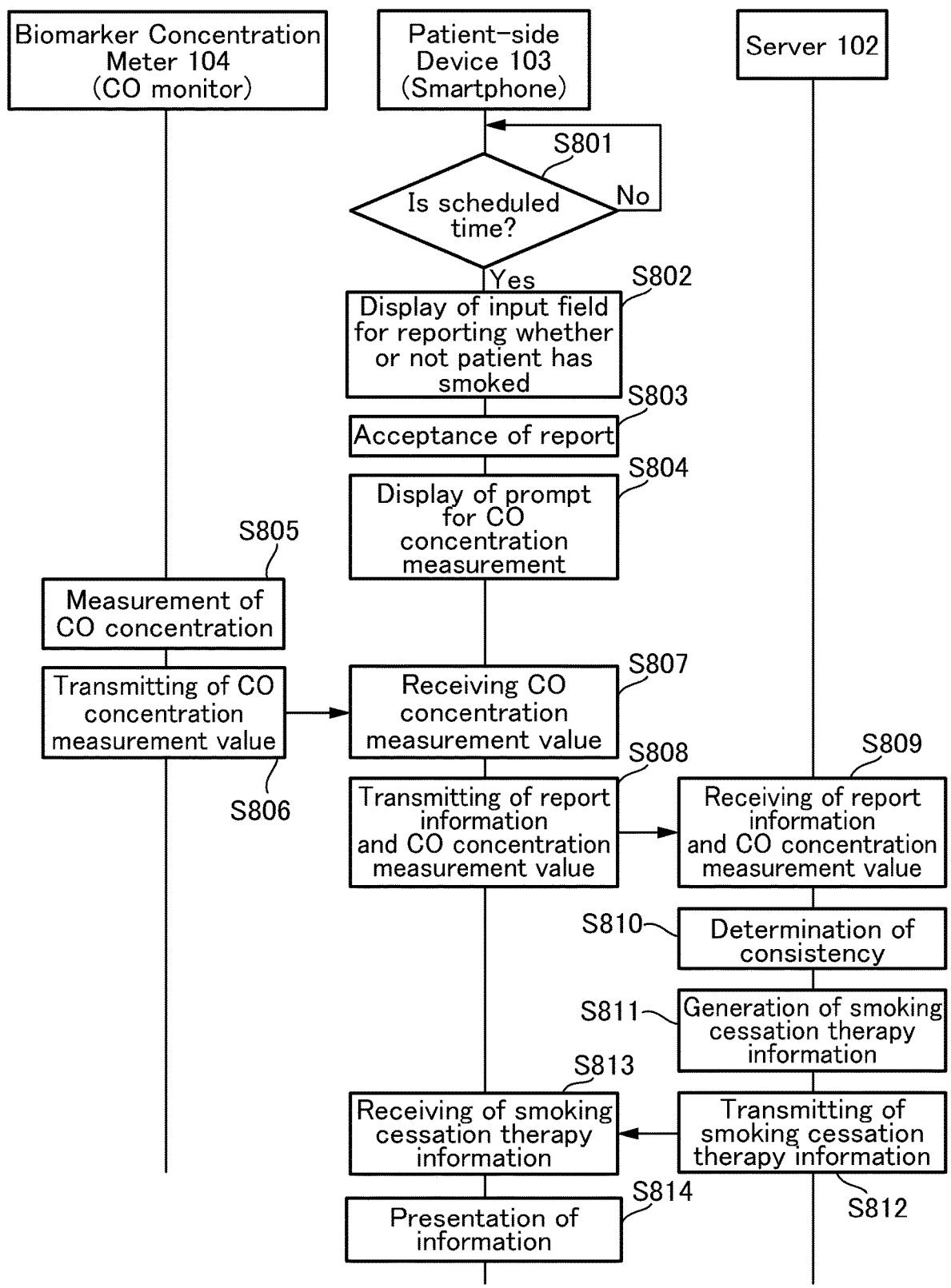
FIG. 8 is a flowchart depicting a process in the system according to the first embodiment and a system according to each of second and third embodiments of the present invention.

In the first embodiment, as depicted in FIG. 8, a patient manipulates the patient-side device 103 which is his/her smartphone, and the CO monitor 104, to input report information indicative of the presence or absence of smoking by the patient, and measure the concentration of CO contained in exhaled breath as a biological sample of the patient. Then, consistency between the report information and a measurement value of the CO concentration is determined, and smoking cessation therapy is performed based on a result of the determination. In the first embodiment, the smoking cessation therapy includes behavioral therapy and cognitive-behavioral therapy. However, in another embodiment, it may also include any other suitable therapy such as coaching.

The patient is requested to report, at given intervals after start of the smoking cessation therapy, the presence or absence of smoking by the patient in each interval. For example, the given interval may be a specific clock time in each day determined by the patient, or may be intervals of two hours, or may be a time zone and the number of times pre-set in the system. At this report timing, the patient is requested to input information on whether he/she has smoked, into the patient-side device 103. In the first embodiment, smoking (smoking behavior) to be reported is defined as smoking since the previous report. Alternatively, it may be defined as smoking behavior within a given period of time. The server 102 may store therein a smoking history of previously reported smokings (smoking behaviors). Upon start of the smoking cessation therapy, a program for executing a process according to one or more embodiments of the present invention is installed in the patient-side device 103, to prompt the patient to input a clock time of once-a-day report. For example, when the patient sets the report clock time to one a day at 22 o'clock, the patient-side device 103 will be kept in a standby state until the set clock time (S801). Then, at the set clock time, the patient-side device 103 displays, on the display section 602 thereof, the message "Have you smoked since the previous recording?" to prompt the patient to input "Yes" or "No" (S802).

According to this prompt, the patient inputs "Yes" or "No", using the input section 603. Upon receiving the input information (S803), the patient-side device 103 displays, on the display section 602, the message "CO concentration will be measured. Please exhale into a mouthpiece of the CO monitor." (S804). When the patient exhales into the mouthpiece of the CO monitor according to the prompt, the CO monitor measures the concentration of CO contained in exhaled breath of the patient (S805), and then transmits the resulting measurement value to the patient-side device 103 by wireless communication (S806). Upon receiving the CO concentration measurement value (S807), the patient-side device 103 transmits the received CO concentration measurement value to the server 102, together with report information input by the patient and indicative of the presence or absence of smoking by the patient (S808).

Upon receiving the CO concentration measurement value and the report information (S809), the server 102 determines consistency between the report information and the CO concentration measurement value (S810). In the first embodiment, the consistency determination is performed by comporting the CO concentration measurement value with a pre-set CO concentration reference value. Generally, it is considered that the concentration of CO contained in exhaled breath of a patient who has smoked is 8.0 ppm or more. Therefore, in the first embodiment, a value of 8.0 ppm is used as the CO concentration reference value serving as a biomarker concentration reference value. Thus, when the CO concentration reference value is equal to or greater than 8.0 ppm, it is determined that the patient has smoked. On the other hand, when the CO concentration reference value is less than 8.0 ppm, it is determined that the patient has not smoked. For example, when the CO concentration reference value is 9.0 ppm although the patient reports that he/she has not smoked, the report information and the CO concentration measurement value are determined to be inconsistent with each other. On the other hand, when the patient reports that he/she has not smoked, and the CO concentration reference value is 5.0 ppm, the report information and the CO concentration measurement value are determined to be consistent with each other. The server 102 may be configured to determine the consistency, including the previous report information. For example, when the previous report information indicates smoking within 48 hours, the current report information may be determined to indicate the presence of smoking by the patient.

Based on a result of the consistency determination, the server 102 generates guidance information for smoking cessation therapy (S811). The server 102 stores, in the storage section, the report information, the result of the consistency determination and the guidance information for smoking cessation therapy, in the form of a smoking cessation therapy list in which the report information, the result of the consistency determination are associated with the guidance information. The smoking cessation therapy list for use in the first embodiment is presented in Table 1.

TABLE 1

| ID | Report Information | Consistency | Guidance information |
|---|---|---|---|
| 1 | 0 | 1 | "Great! You could keep from smoking today! Please continue the ongoing substitute behavioral therapy (one type of behavioral therapy) based on chewing some gum, to keep up smoking cessation." |

TABLE 1-continued

| ID | Report Information | Consistency | Guidance information |
|---|---|---|---|
| 2 | 0 | 0 | "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?" |
| 3 | 1 | 1 | "Today is the fourth day of smoking cessation, and is still in a period where a withdrawal symptom strongly appears. Why don't you think again whether the ongoing behavioral therapy sufficiently achieves an effect? The substitute behavioral therapy (one type of behavioral therapy) based on chewing some gum has been continued. If you do not feel right about this therapy, it may be switched to a substitute behavioral therapy based on drinking sugar-free soda water." |
| 4 | 1 | 0 | "Unfortunately you have smoked one cigarette. Although you restarted smoking, the expression of nicotinic receptors is considered to be not yet so strong. Thus, it is not too late to discard cigarettes and an ash tray (environment improving approach: one type of behavioral therapy) so as to suppress an urge to smoke next one cigarette." |
| - - - | - - - | - - - | - - - |

The smoking cessation therapy list in the first embodiment includes IDs of various therapies, report on smoking, consistency, and guidance information. As regards "report information", "0" is assigned to therapy to be performed when a patient reports that he/she has not smoked, and "1" is assigned to therapy to be performed when the patient reports that he/she has smoked. As regards "consistency", "1" is assigned to therapy to be performed when the report information and the CO concentration measurement value are consistent with each other, and "0" is assigned to therapy to be performed when the report information and the CO concentration measurement value are inconsistent with each other.

Based on a result of the consistency determination, the server 102 selects appropriate guidance information from the smoking cessation therapy list presented in Table 1. For example, in the case where the report information indicates the absence of smoking by the patient, and the CO concentration measurement value is 5.0 ppm, i.e., CO concentration measurement value<CO concentration reference value (8.0 ppm), both of the report information and the CO concentration measurement value indicate the absence of smoking by the patient, and therefore they are consistent with each other. In this case, as one example, ID=1 corresponding to report-on-smoking=0 (absence of smoking) and consistency=1 (consistent) is selected, and smoking cessation therapy information for presenting the following message is generated as guidance information: "Great! You could keep from smoking today! Please continue the ongoing substitute behavioral therapy (one type of behavioral therapy) based on chewing some gum, to keep up smoking cessation."

When the report information indicative of No and the CO concentration reference value are consistent with each other, it is determined that smoking recession can be continued, and the ongoing therapy (in this example, substitute behavioral therapy (one type of behavioral therapy) based on chewing some gum) achieves an effect. Thus, the guidance information instructs the patient to continue the ongoing behavioral therapy. For example, the server 102 may store therein smoking cessation therapies suggested to the patient that he/she implements them, in the form of a therapy history. This makes it possible to specify smoking cessation therapy which is currently performed by the patient.

On the other hand, in the case where, although the report information indicates the absence of smoking by the patient, the CO concentration measurement value is 10.0 ppm, i.e., CO concentration measurement value>CO concentration reference value (8.0 ppm), the report information indicative of the absence of smoking by the patient and the CO concentration measurement value indicative of the presence of smoking by the patient are inconsistent with each other. In this case, as one example, ID=2 corresponding to report-on-smoking=0 (absence of smoking) and consistency=0 (inconsistent) is selected, and smoking cessation therapy information for presenting the following guidance information is generated: "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?"

It is known that there are many cases where a patient during smoking cessation therapy tells a lie that he/she has not smoked when smoked despite being under smoking cessation therapy. Such a patient tells the lie due to erroneous cognition, i.e., understanding, as a negative event, the fact that he/she has restarted smoking despite being prohibited. If this state is left untreated, the patient thinks that he/she cannot continue smoking cessation therapy any more, or it is impossible for him/her to accomplish smoking cessation therapy, and gives up continuing the smoking cessation therapy, in many cases.

In one or more embodiments of the present invention, by detecting a false report regarding the presence or absence of smoking by the patient, it is possible to detect that the patient has such erroneous cognition. Then, by presenting guidance information for correcting the erroneous cognition, it is possible to lower a barrier against re-attempting to quit smoking, from the state just after restarting smoking. After the patient gives up continuing the smoking cessation therapy and returns to habitual smoking, it becomes extremely difficult to correct the cognition and motivate the patient to re-attempt to accomplish smoking cessation therapy. In one or more embodiments of the present invention, by detecting that a patient has restarted smoking and that the patient has erroneous cognition, at an adequate timing, and then correcting the cognition, it is possible to effectively assist the patient in keeping from returning to habitual smoking and continuing smoking cessation therapy (cognitive-behavioral therapy).

Further, in the case where the report information indicates the presence of smoking by the patient, and the CO concentration measurement value is equal to or greater than 8.0 ppm, i.e., indicates the presence of smoking by the patient, the report information indicative of the presence of smoking by the patient and the CO concentration measurement value indicative of the presence of smoking by the patient are consistent with each other. In this case, as one example, ID=3 corresponding to report information=1 (presence of smoking) and the consistency=1 (consistent) is selected, and guidance information for suggesting changing the current behavioral therapy which might be not so effective is presented to the patient as follows: "Today is the fourth day of smoking cessation, and is still in a period where a withdrawal symptom strongly appears. Why don't you think again whether the ongoing behavioral therapy sufficiently achieves an effect? The substitute behavioral therapy (one type of behavioral therapy) based on chewing some gum has been continued. If you do not feel right about this therapy, it may be switched to a substitute behavioral therapy based on drinking sugar-free soda water."

Further, in the case where, although the report information indicates the presence of smoking by the patient, the CO concentration measurement value is not equal to or greater than the CO concentration reference value, ID=4 corresponding to report information=1 (presence of smoking) and the consistency=0 (inconsistent) is selected, and the following guidance information is presented: "Unfortunately you have smoked one cigarette. Although you restarted smoking, the expression of nicotinic receptors is considered to be not yet so strong. Thus, it is not too late to discard cigarettes and an ash tray (environment improving approach: one type of behavioral therapy) so as to suppress an urge to smoke next one cigarette."

The guidance information to be presented in this case is designed to enable the patient to understand that a serious negative influence as the patient thinks does not occur even after restarting smoking, and prevent the patient to have erroneous cognition that there is no meaning in continuing smoking cessation therapy any more. Further, the report information indicative of the presence of smoking by the patient shows that a sufficient effect is not obtained only by the ongoing smoking cessation therapy. Thus, as one example, the guidance information is presented to implement behavioral therapy based on discarding cigarettes and an ash tray, which is effective when restarting smoking, to thereby encourage the patient not to smoke further.

For example, the server 102 may store therein a smoking cessation start date as a therapy history. This makes it possible to generate guidance information more appropriate to each smoking cessation stage. Further, the server 102 may store therein ID of smoking cessation therapy which has been performed, as a smoking cessation therapy history. This makes it possible to specify smoking cessation therapy which is currently ineffective, and select ID of smoking cessation therapy which has not yet been performed.

When the server 104 transmits the generated smoking cessation therapy information to the patient-side device 103 (S812), the patient-side device 103 receives the smoking cessation therapy information (S813), and displays the guidance information on the display section 602 based on the smoking cessation therapy information (S814). Alternatively, the guidance information may be presented to the patient by means of voice from a voice output section such as a speaker.

The CO monitor 104 may be configured to, upon measuring the CO concentration, generate a time stamp indicative of a clock time of the measurement, and transmit it to the patient-side device 103 together with the CO concentration measurement value, and the patient-side device 103 may be configured to transmit them to the server 102 so as to check whether the CO concentration was measured at an appropriate clock time such as a pre-set measurement clock time. It is assumed that a patient attempts to falsify the CO concentration measurement clock time to fake the absence of smoking although the patient has smoked. In such a situation, if there is no information indicative of the measurement clock time, or the information indicative of the measurement clock time is self-reported by means of manual input by the patient, it becomes impossible to properly determine the consistency. The CO monitor may be configured to automatically generate a time stamp at a timing of completion of the CO concentration measurement, and transmit the time stamp to the server 102 via the patient-side device 103. In this case, the server 102 can perform the consistency determination based on an accurate measurement clock time.

The time stamp may be a time stamp indicative of a clock time at which the CO monitor transmits the CO concentration measurement value to the patient-side device 103, or may be generated by the patient-side device 103, based on a clock time at which the patient-side device 103 receives the CO concentration measurement value or transmits it to the server 102, or may be generated at a timing when the server 102 receives the CO concentration measurement value. In the case where the patient-side device 103 is constructed as an integral structure with the CO sensor, the patient-side device 103 can generate a time stamp at a timing of completion the CO concentration measurement.

In the first embodiment, the concentration of CO contained in exhaled breath of the patient is used as the biomarker indicative of the smoking state. Alternatively, the concentration of cotinine contained in saliva of the patient may also be used to implement the embodiments of the present invention. In case of using the cotinine concentration, a cotinine concentration meter may be used, as a substitute for the CO monitor, and the presence of smoking may be determined, for example, when a measurement value of the cotinine concentration is equal to or greater than 1.4 ng/ml.

The use of the system according to the first embodiment makes it possible to, based on the report information indicative of the presence or absence of smoking of a patient, and the CO concentration measurement value, check the presence or absence of smoking by the patient, while determining whether or not the patient makes a false report, and select and implement appropriate therapy suited to a state of the patient, at an appropriate timing.

Second Embodiment

A system according to a second embodiment of the present invention is different from the system according to the first embodiment, in that the report information indicative of the presence or absence of smoking of a patient (whether or not a patient has smoked) includes the number of cigarettes smoked and a smoking timing, instead of simple information about the presence or absence of smoking by the patient, and the consistency determination also comprises determining whether or not there is consistency between the report information including the number of cigarettes smoked and the smoking timing, and a biomarker concentration measurement value. When the report information includes information indicating that the number of cigarettes smoked is 0, it can be understood to indicate the absence of smoking, whereas, when the report information includes information indicating that the number of cigarettes smoked is one or more, it can be understood to indicate the presence of smoking. Differences from the first embodiment will be mainly described below.

As with the first embodiment, in the second embodiment, a smartphone and a CO monitor are used, respectively, as the patient-side device 103 and the biomarker concentration meter 104, to execute the processing as depicted in FIG. 8. As described later, specific processing are different from that in the first embodiment. At a clock time pre-set by a patient, the patient-side device 103 displays, on the display section 602 thereof, the message "Have you smoked since the previous report?" to prompt the patient to input "Yes" or "No" (S802). When there is the input "Yes" from the patient, the patient-side device 103 further presents the message "What time and how many cigarettes did you smoke? Please input the number of cigarettes smoked and a smoking timing" to prompt the patient to input the number of cigarettes smoked (smoked cigarette number) and the smoking timing. As an input method, it is conceivable that the patient is prompted to input the smoked cigarette number at each smoking timing (e.g., 5 hours before: 2 cigarettes, 3 hours before: one cigarette). However, any other suitable input method may be employed as long as it is capable of specifying the smoked cigarette number and the smoking timing. Upon receiving the report information, the patient-side device 103 prompts the patient to perform the CO concentration measurement, so that the CO concentration in exhaled breath is measured, and the measured CO concentration value is transmitted to the server 102 (S804 to S808).

Upon receiving the report information and the CO concentration measurement value (S809), the server 102 determines consistency between the report information and the CO concentration measurement value (S810). In the second embodiment, the consistency determination is performed by comporting the CO concentration measurement value with an upper limit value of the CO concentration as a biomarker concentration reference value. The upper limit value of the CO concentration is determined based on the smoked cigarette number and the smoking timing each indicated by the report information, and an attenuation function of the CO concentration. In the second embodiment, a time attenuation function of the concentration of CO contained in exhaled breath of a patient who has smoked is defined as follows:

$$\text{CO concentration value } (0) = K \times \text{Smoked cigarette number } N \quad (1)$$

$$\text{CO concentration value } (t) = \frac{\text{CO concentration value } (t-1) - P}{2^{1/H}} + P(t > 0) \quad (2)$$

The formula (1) represents an initial value of the concentration of CO estimated to be contained in exhaled breath of a patient just after smoking. K denotes a concentration value of CO contained in exhaled breath of the patient just after smoking one cigarette. In the second embodiment, K is set to 18 ppm. However, it is to be understood that K may be set based on various factors such as a type of tobacco in a cigarette smoked. The smoked cigarette number N indicates the number of cigarettes smoked at the smoking timing.

A concentration of CO estimated to be contained in exhaled breath of the patient since then attenuates as the attenuation function represented by the formula (2). P denotes a minimum value of the concentration of CO contained in exhaled breath of a person deemed as a smoker. The concentration of CO contained in exhaled breath of a patient who has smoked is considered to be equal to or greater than 8.0 ppm. Thus, in the second embodiment, P is set to 8.0 ppm. t denotes an elapsed time from the smoking timing. H denotes the half-life of the CO concentration. The half-life of the concentration of CO contained in exhaled breath of a patient just after smoking is generally considered to be in the range of 3 hours to 6 hours. Thus, in the second embodiment, the half-life H for a function for setting the upper limit value of the CO concentration is set to 6 hours.

Figure 9:
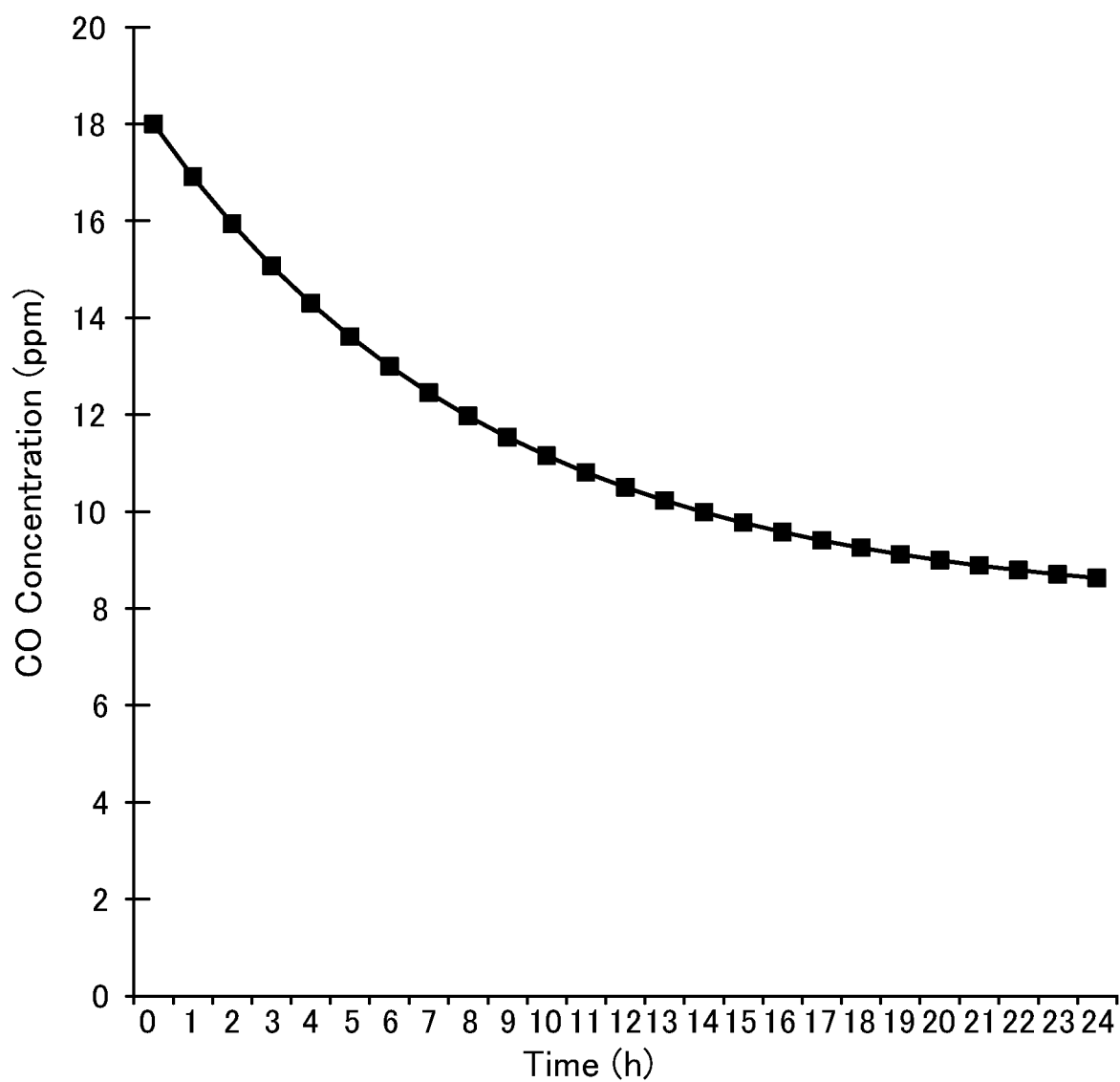
FIG. 9 is a graph presenting an attenuation function of a CO concentration in the system according to the second embodiment.

FIG. 9 depicts an attenuation curve of the CO concentration values obtained based on the formulas (1) and (2) under the above conditions. FIG. 9 shows that the CO concentration value is 18 ppm when t=0, and gradually attenuates therefrom over time. In FIG. 9, the CO concentration values were calculated based on the formulas (1) and (2) at intervals of one hour, and plotted. Then, curves between adjacent ones of the plots were determined by linear interpolation. Alternatively, any other interpolation method may be used, and an approximate curve may be used as the attenuation curve of the CO concentration values. Further, any other suitable attenuation function may be used as long as it expresses a time attenuation of the concentration of CO contained in exhaled breath of a patient.

Further, in the case where smoking is performed at intervals of a certain time, a CO concentration value at an elapsed time T from an initial one of a plurality of timings of smoking can be estimated based on the following formula (3), and a CO concentration value since then can be calculated using the aftermentioned formula (2). NT denotes the number of cigarettes smoked at the elapsed time T.

$$\text{CO concentration value } (T) = \frac{\text{CO concentration value } (T-1) - P}{2^{1/H}} + P + K \times N_T \quad (3)$$

Figure 10:
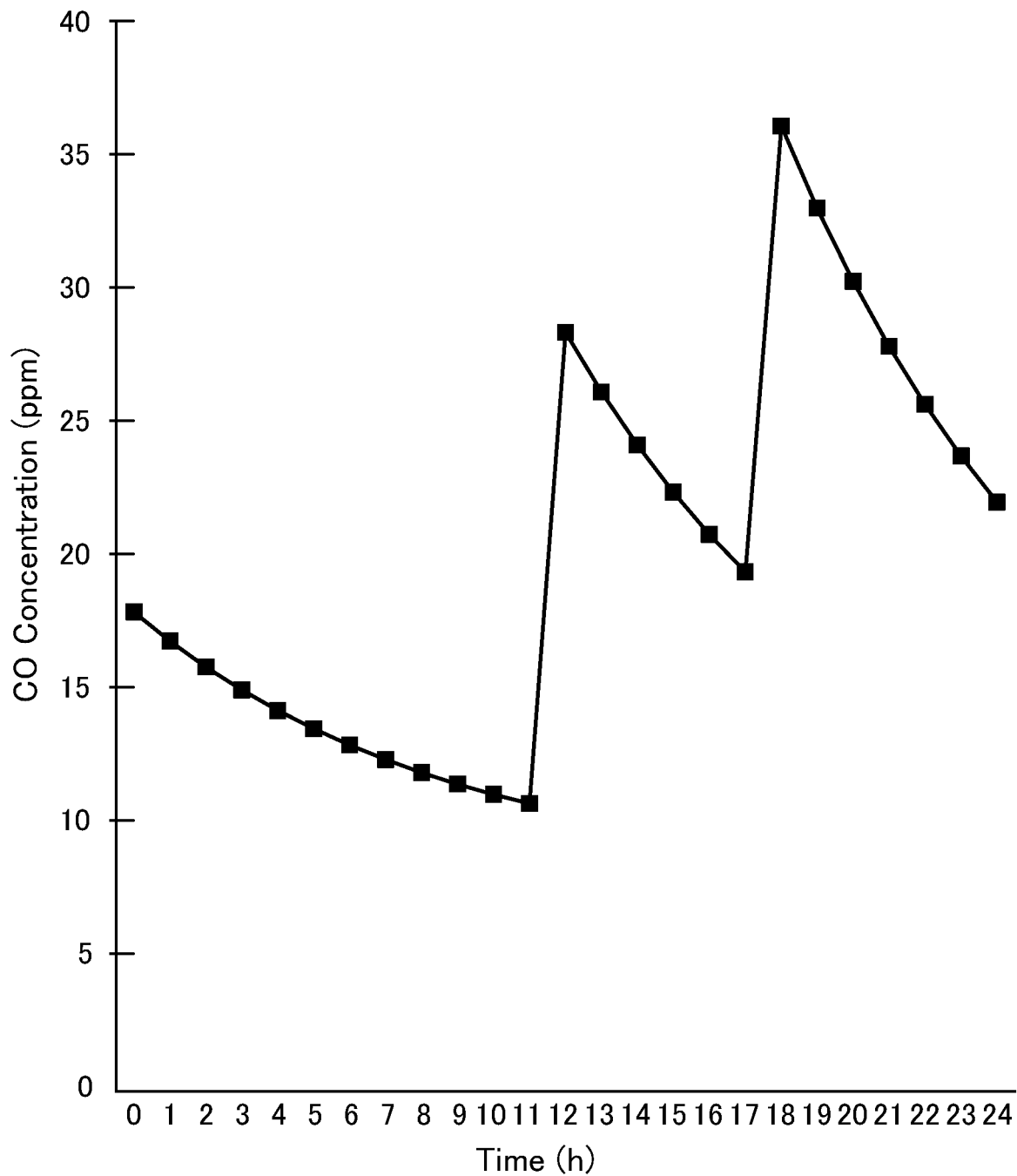
FIG. 10 is a graph presenting another attenuation function of the CO concentration in the system according to the second embodiment.

As one example, FIG. 10 depicts an attenuation curve of the CO concentration values in the case where the half-life H is set to 6 hours, and 2 cigarettes are smoked, respectively, after 12 hours and after 18 hours from initial smoking (0 hour). FIG. 10 shows that 18 ppm is added at each timing of t=12 hours and t=18 hours. Alternatively, a CO concentration value i is calculated based on the formula (2) at each smoking timing, and a sum of the CO concentration values i can be used as the attenuation function of the CO concentration value, as represented by the following formula (4). In this case, i denotes a counter number of smoking timing. Specifically, the first smoking timing is 1, and the second smoking timing is 2. Z denotes a total number of smoking timings. Ti denotes an elapsed time at a smoking timing i from the first smoking timing. For example, in the case where smoking is performed at three timings: 0 hours; 12 hours; and 18 hours, Z=3, $T_1=0$, $T_2=12$, $T_3=18$. Then, a CO concentration value 1 arising from the first smoking is calculated based on the formula (1), and a CO concentration value 2 arising from smoking at a timing after the elapse of 12 hours and a CO concentration value 3 arising from smoking at a timing after the elapse of 18 hours are calculated based on the formula (2), and two results of the calculations are added together.

$$\text{CO concentration value }(t) = \sum_{i=1}^{Z} \text{CO concentration } value_i(t - T_i) \quad (4)$$

In the second embodiment, a CO concentration value set based on the attenuation function of the CO concentration under the condition that the half-life H is 6 hours is used as the upper limit value of the CO concentration. The upper limit value of the CO concentration means an upper limit value of the CO concentration to determine a patient smoked the reported number of cigarettes at the reported smoking timing. Assume a situation where a CO concentration value greater than the upper limit value of the CO concentration is measured. This situation is considered to mean that a patient subjected to the measurement has smoked cigarettes in a number greater than the reported number. Although values to be calculated by the attenuation function of the CO concentration represented by the formulas (1) and (2) are discrete, interpolation such as linear interpolation can be utilized to form then into a continuous attenuation curve as depicted in FIG. 9. Then, it is possible to set the upper limit value of the CO concentration based on this attenuation curve. Alternatively, an approximate curve may be used as the attenuation curve.

The smoked cigarette number and the smoking timing to be assigned to the attenuation function of the CO concentration are set based on the report information from the patient. That is, in the second embodiment, the upper limit value of the CO concentration is set based on the attenuation function of the CO concentration, and the smoked cigarette number and the smoking timing each reported by the patient. Then, by comparing the set upper limit value of the CO concentration with the CO concentration measurement value, consistency between the report information and the CO concentration measurement value is determined. In operation of setting the upper limit value of the CO concentration, the upper limit value of the CO concentration may be set based on only the latest report information, or may be set based on all or part of a plurality of pieces of report information reported within a given period of time, such as a period of time in which CO is detectable. In the second embodiment, operation of the system will be described by taking as an example the former case where the upper limit value of the CO concentration is set based on only the latest report information.

For example, in the case where the report information from the patient indicates that the patient smoked one cigarette 6 hours before, the upper limit value of the CO concentration is read as 13 ppm, based on the attenuation function of the CO concentration. Further, assume that the CO concentration measurement value is 12.0 ppm. In this case, comparing the CO concentration measurement value being 12.0 ppm with the upper limit value of the CO concentration being 13 ppm, it is determined that the CO concentration measurement value is equal to or less than the upper limit value of the CO concentration. When the CO concentration measurement value is equal to or less than the upper limit value of the CO concentration, the report information and the CO concentration measurement value are determined to be consistent with each other. Subsequently, based on a result of this determination, the server 102 generates guidance information for smoking cessation therapy for the patient (S811). Then, the guidance information is transmitted to the patient-side device 103, and presented to the patient in the patient-side device 103 (S812 to S814). The server 102 stores therein the report information, the result of the consistency determination and the guidance information for smoking cessation therapy, in the form of a smoking cessation therapy list in which the report information, the result of the consistency determination are associated with the guidance information. The smoking cessation therapy list for use in the second embodiment is presented in Table 2.

TABLE 2

| ID | Report Information | Consistency | Guidance information |
|---|---|---|---|
| 1 | 0 | 1 | "Great! You could keep from smoking today! Please continue the ongoing substitute behavioral therapy (one type of behavioral therapy) based on chewing some gum, to keep up smoking cessation." |
| 2 | >=0 | 0 | "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?" |
| 3 | >=1 | 1 | "Today is the fourth day of smoking cessation, and is still in a period where a withdrawal symptom strongly appears. Why don't you think again whether the ongoing behavioral therapy sufficiently achieves an effect? The substitute behavioral therapy (one type of behavioral therapy) based on chewing some gum has been continued. If you do not feel right about this therapy, it may be switched to a substitute behavioral therapy based on drinking sugar-free soda water." |

TABLE 2-continued

| ID | Report Information | Consistency | Guidance information |
|---|---|---|---|
| 4 | 1 | 1 | "Unfortunately you have smoked one cigarette. Although you restarted smoking, the expression of nicotinic receptors is considered to be not yet so strong. Thus, it is not too late to discard cigarettes and an ash tray (environment improving approach: one type of behavioral therapy) so as to suppress an urge to smoke next one cigarette." |
| --- | --- | --- | --- |

The numeral presented in "Report Information" in Table 2 denotes smoking cessation therapy corresponding to the smoked cigarette number reported by the patient. That is, the numerals "0", "1" and "2" in "Report Information" mean, respectively, smoking cessation therapies to be performed for: a report that the patient has not smoked; a report that the patient has smoked one cigarette; and a report that the patient has smoked 2 cigarettes. Further, the numerals ">=0" and ">=1" in "Report Information" mean, respectively, smoking cessation therapies to be performed for any report (i.e., all reports) that the patient has smoked 0 or more cigarettes; and any report that the patient has smoked one or more cigarettes. For example, when the patient makes a report that he/she has smoked one cigarette, smoking cessation therapy is appropriately selected from a group of smoking cessation therapies to which the numeral "1" or ">=1" in "Report Information" is assigned. The numerals in "Consistency" are the same as those in Table 1.

As one example, in the cases where the report information indicates that the patient smoked one cigarette 6 hours before, and the CO concentration measurement value is equal to or less than the upper limit value of the CO concentration, it is evaluated that smoking was actually performed in the same manner as that reported by the patient. In this case, from the smoking cessation therapy list presented in Table 2, smoking cessation therapy having the numeral "1" or ">=1" (the presence of smoking of one or more cigarettes) in "Report Information" and the numeral "1" (consistent) in "Consistency" is selected. In this example, ID=4 is selected, and smoking cessation therapy information for presenting the following guidance information to the patient is generated: "Unfortunately you have smoked one cigarette. Although you restarted smoking, the expression of nicotinic receptors is considered to be not yet so strong. Thus, it is not too late to discard cigarettes and an ash tray (environment improving approach: one type of behavioral therapy) so as to suppress an urge to smoke next one cigarette." (S811).

That is, from the report information and the CO concentration measurement value, it is ascertained that the smoked cigarette number is still only one although the patient has smoked. The guidance information to be presented in this case is designed to enable the patient to understand that the patient is still at a level capable of catching up on, although he/she has smoked, and prevent the patient to have erroneous cognition that there is no meaning in continuing smoking cessation therapy any more. Further, the report information indicative of the presence of smoking shows that a sufficient effect is not obtained only by the ongoing smoking cessation therapy. Thus, as one example, the guidance information is presented to implement behavioral therapy based on discarding cigarettes and an ash tray, which is effective when restarting smoking, to thereby encourage the patient not to smoke further. In this way, it becomes possible to perform appropriate smoking cessation therapy based on the smoked cigarette number.

On the other hand, in the case where the CO concentration measurement value is equal to or greater than the upper limit value of the CO concentration, it is evaluated that the smoked cigarette number is underreported. This underreporting is made probably because the patient understands smoking during smoking cessation therapy as a negative event. Thus, ID=2 having the numeral ">=0" in "Report Information" and the numeral "0" in "Consistency" is performed to present the following guidance information: "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?", to thereby correct the erroneous negative cognition. In the second embodiment, the CO concentration reference value is set based on the smoked cigarette number and the smoking timing. Thus, it becomes possible to detect a false report in terms of the smoked cigarette number, and detect negative cognition regarding smoking even in the case where the patient reports the presence of smoking.

In the second embodiment, the concentration of CO contained in exhaled breath of the patient is used as the biomarker indicative of the smoking state. Alternatively, the concentration of cotinine contained in saliva of the patient may also be used to implement the embodiments of the present invention. In case of using the cotinine concentration, the consistency determination can be performed based on a measured cotinine concentration and an attenuation function of the cotinine concentration. The half-life of the cotinine concentration is considered to be in the range of 15 to 30 hours. The attenuation function of the cotinine concentration for setting an upper limit value of the cotinine concentration based thereon can be defined as follows. However, it is to be understood that any other suitable attenuation function of the cotinine concentration may be used as long as it expresses a time attenuation of the concentration of cotinine contained in saliva of the patient.

$$\text{Cotinine concentration value } (0) = L \times \text{Smoked cigarette number } N \quad (5)$$

$$\text{Cotinine concentration value } (t) = \frac{\text{Cotinine concentration value } (t-1) - Q}{2^{1/C}} + Q(t > 0) \quad (6)$$

Further, in the case where smoking is performed at intervals of a certain time, a cotinine concentration value at an elapsed time T from an initial smoking can be calculated using the following formula (7), and a cotinine concentration value since then can be calculated using the above formula (6). Then, a cotinine concentration value calculated based on the smoked cigarette number and the smoking timing indicated by the report information, and the attenuation function of the cotinine concentration is used as an upper limit value of the cotinine concentration. L denotes a concentration value of cotinine contained in saliva of the patient just after smoking one cigarette. Q denotes a minimum value of the concentration of cotinine contained in saliva of a person deemed as a smoker. C denotes the half-life of the cotinine concentration.

$$\text{Cotinine concentration value }(T) = \frac{\text{Cotinine concentration value }(T-1) - Q}{2^{1/C}} + Q + L \times N_T \quad (7)$$

Figure 11:
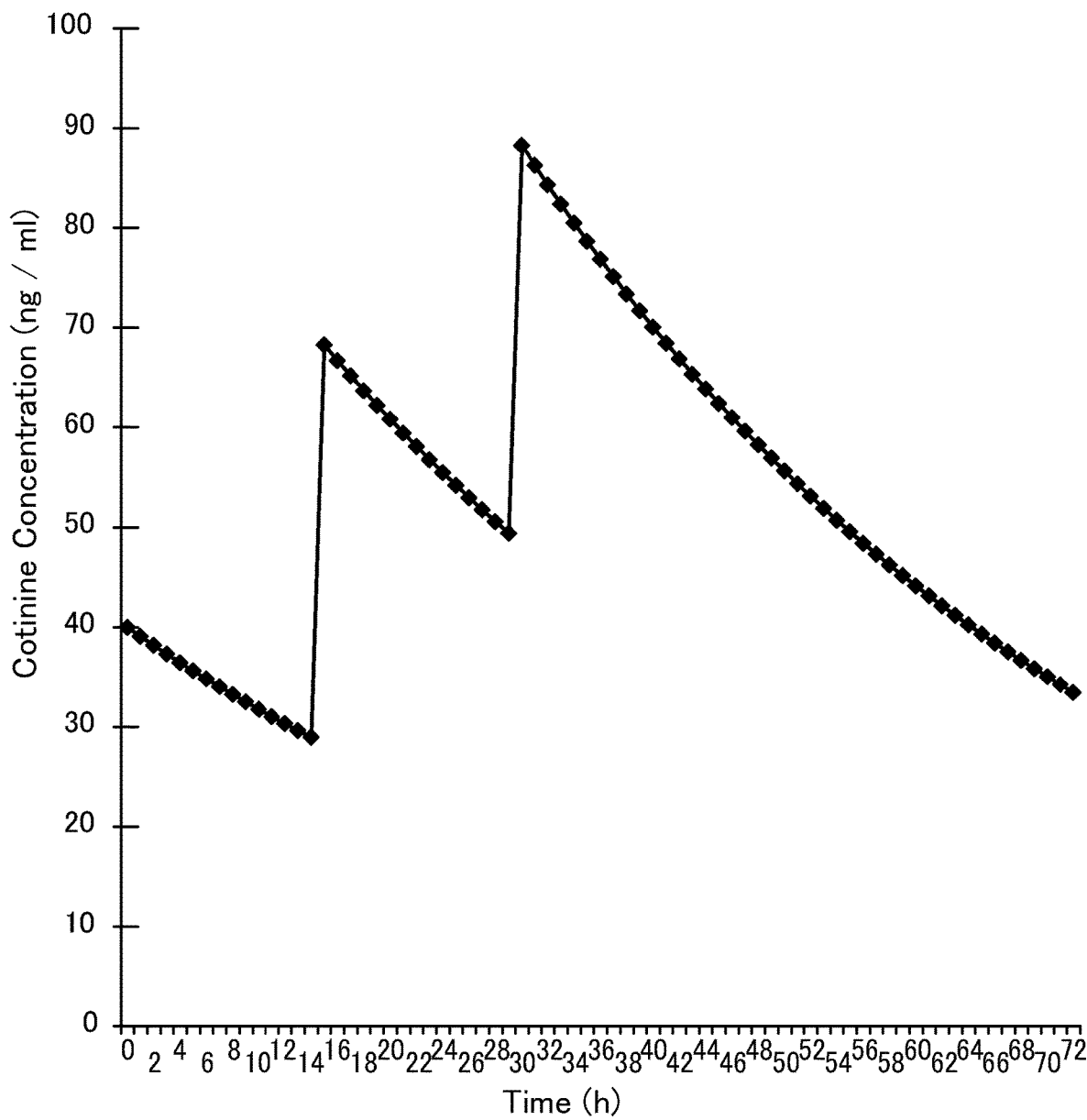
FIG. 11 is a graph presenting an attenuation function of a nicotine concentration in the system according to the second embodiment.

As one example, FIG. 11 depicts an attenuation curve of the cotinine concentration values in the case where: an initial value of the cotinine concentration value L=40 ng/ml; Q=0; half-life C=30 hours; and one cigarette is smoked, and then 2 cigarettes are smoked, respectively, after 15 hours and after 48 hours. In this example, for the sake of simplifying calculation, Q is approximated as 0. Further, as with the CO concentration, an attenuation value is calculated based on the formula (6) at each smoking timing, and a sum of the cotinine concentration values can be used as the attenuation function of the cotinine concentration value. The cotinine concentration has a half-life longer than that of the CO concentration, so that it becomes possible to perform the consistency determination over a longer period of time.

Third Embodiment

In the second embodiment, the consistency determination is performed based on only the upper limit value of the CO concentration. Differently, in the third embodiment, the consistency determination is performed additionally based on a lower limit value of the CO concentration as the biomarker concentration reference value. The lower limit value of the CO concentration means a lower limit value of the CO concentration to determine that the reported number of cigarettes is smoked at the reported smoking timing. Differences from the first and second embodiments will be mainly described below.

As with the first and second embodiments, in the third embodiment, a smartphone and a CO monitor are used, respectively, as the patient-side device 103 and the biomarker concentration meter 104, to execute the processing as depicted in FIG. 8. As described later, specific processing are different from those in the first and second embodiments. At a clock time pre-set by a patient, the patient-side device 103 requests the patient to input the report information indicative of the present or absence of smoking by the patient, and, when the patient has smoked, to input the smoked cigarette number and the smoking timing, whereafter, when accepting the report information, the patient-side device 103 prompts the patient to perform the CO concentration measurement for measuring the concentration of CO in exhaled breath of the patient, and transmits a measured CO concentration value to the server 102 (S801 to S808).

Upon receiving the report information and the CO concentration measurement value (S809), the server 102 determines consistency between the report information and the CO concentration measurement value (S810). In the third embodiment, the consistency determination is performed by comporting the CO concentration measurement value with the upper limit value of the CO concentration and the lower limit value of the CO concentration. Each of the upper limit value of the CO concentration and the lower limit value of the CO concentration can be determined based on the smoked cigarette number and the smoking timing each indicated by the report information, and the attenuation function of the CO concentration. As mentioned above, the half-life of the concentration of CO contained in exhaled breath of a patient just after smoking is generally considered to be in the range of 3 hours to 6 hours. Further, the concentration of CO contained in exhaled breath of a patient who has smoked is considered to be equal to or greater than 8.0 ppm.

Figure 12:
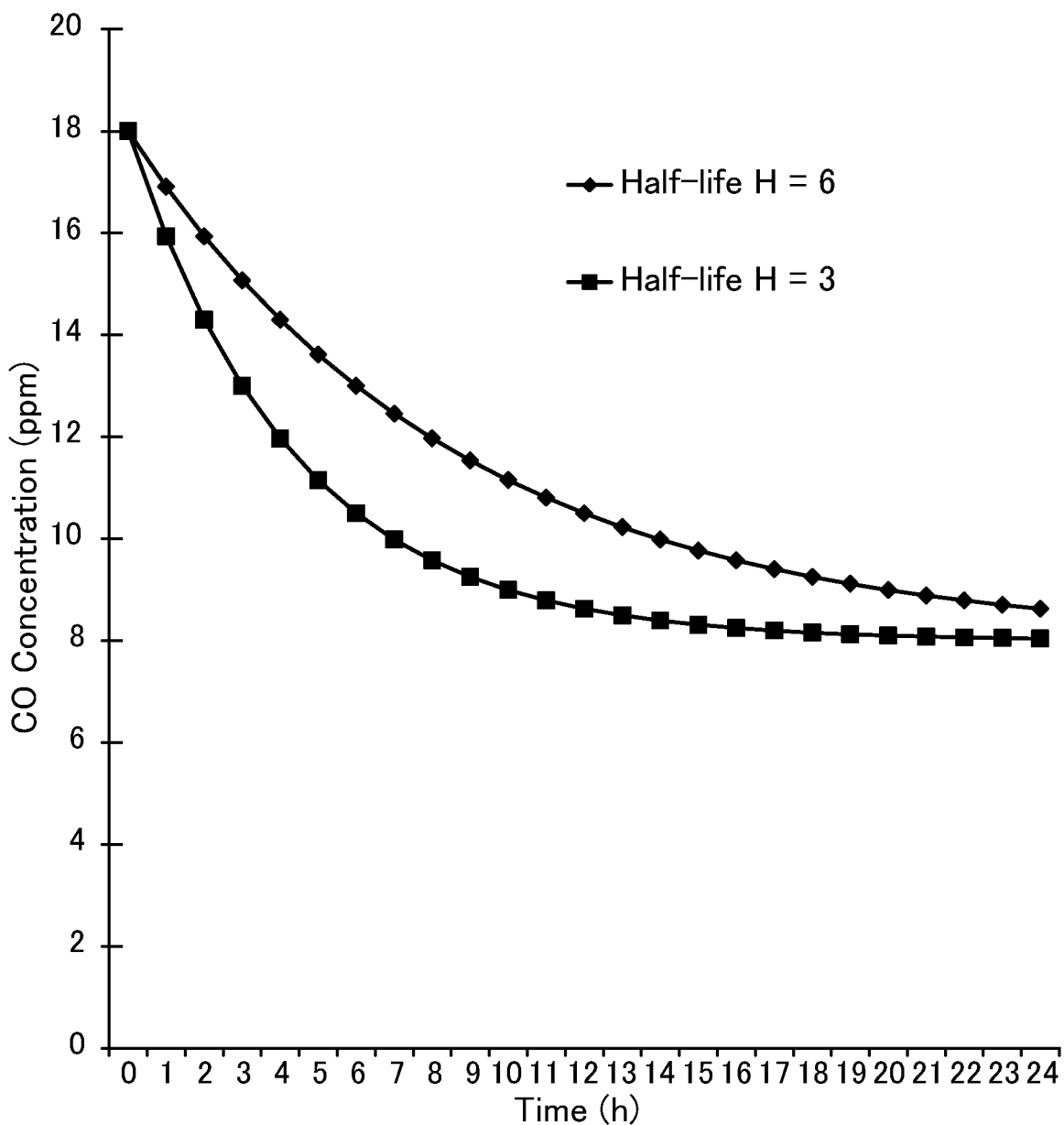
FIG. 12 is a graph presenting an attenuation function of the CO concentration in the system according to the third embodiment.

Based on the above assumption, in the third embodiment, in addition to the upper limit value of the CO concentration, the lower limit value of the CO concentration is set based on the aforementioned formulas (1) and (2). A first attenuation function of the CO concentration obtained when half-life H=6 is used to set the upper limit value of the CO concentration, and a second attenuation function of the CO concentration obtained when half-life H=3 is used to set the lower limit value of the CO concentration. FIG. 12 depicts attenuation curves of the CO concentration set based on these attenuation functions of the CO concentration. In the third embodiment, the initial value K for the upper and lower limit values of the CO concentration is set to 18 ppm, as in the second embodiment. Alternatively, the initial value K may be set to different values in the first attenuation function of the CO concentration for the upper limit value of the CO concentration, and the second attenuation function of the CO concentration for the lower limit value of the CO concentration. The upper and lower limit values of the CO concentration are set using the smoked cigarette number and the smoking timing reported by the patient, the first attenuation function of the CO concentration (H=6 hours) for the upper limit value of the CO concentration, and the second attenuation function (H=3 hours) of the CO concentration for the lower limit value of the CO concentration. When the CO concentration measurement value lies between the two attenuation curves of the CO concentration in FIG. 12, this relation means that the report information and the CO concentration measurement value are consistent with each other.

Further, in the case where smoking is performed at intervals of a certain time, as regards the lower limit value of the CO concentration, a CO concentration value at an elapsed time T from an initial smoking can be estimated using the formula (3) in which the half-life is set to 3 hours, and a CO concentration value since then can be estimated using the formula (2) in which the half-life is set to 3 hours, so as to calculate the first attenuation function of the CO concentration, as with the upper limit value of the CO concentration.

Figure 13:
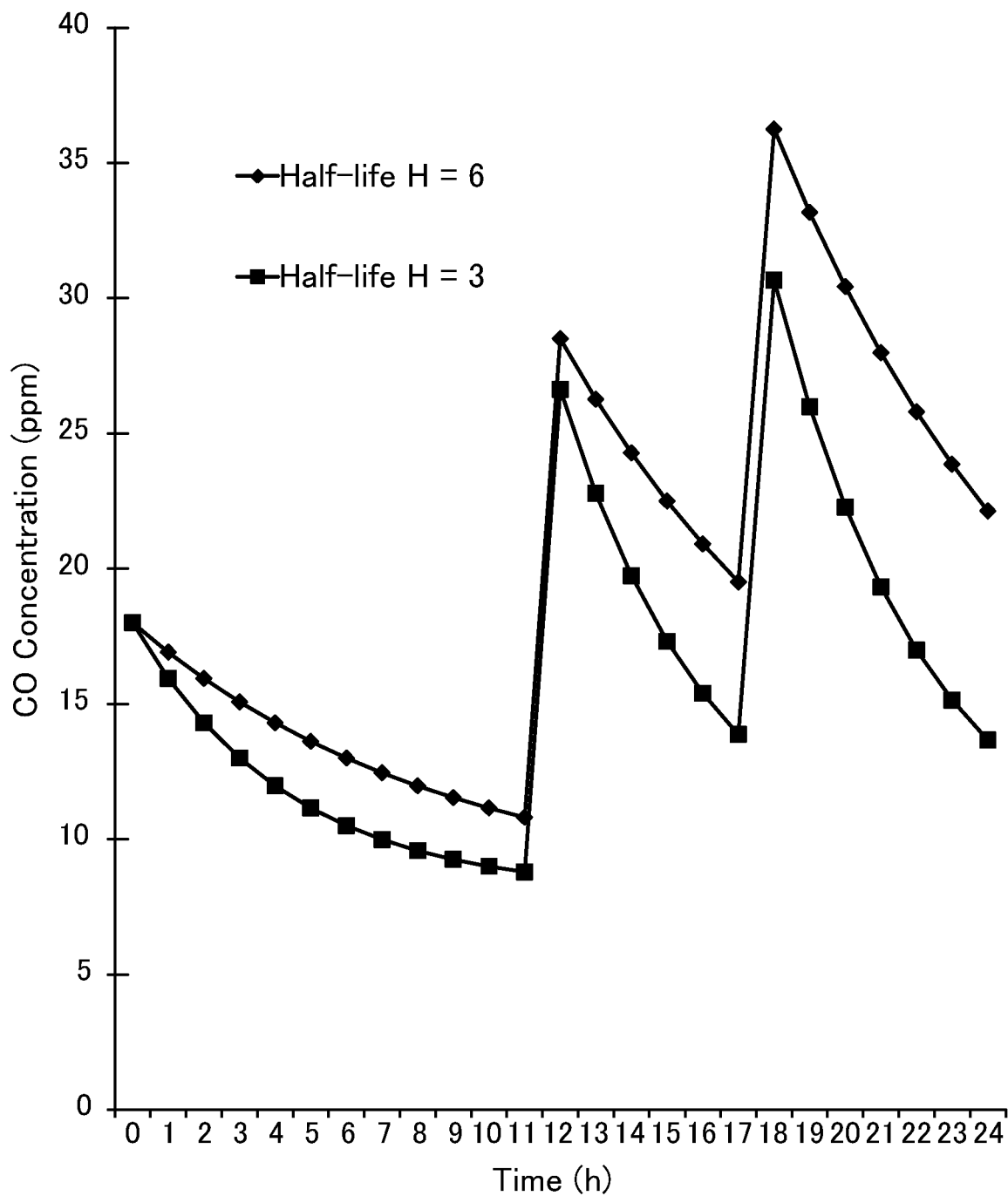
FIG. 13 is a graph presenting another attenuation function of the CO concentration in the system according to the third embodiment.

As one example, FIG. 13 depicts attenuation curves of the CO concentration values for the upper and lower limit values of the CO concentration, in the case where 2 cigarettes are smoked, respectively, after 12 hours and after 18 hours from initial smoking (0 hour). FIG. 13 shows that 18 ppm is added at each timing of t=12 hours and t=18 hours.

In the third embodiment, based on the first and second attenuation functions of the CO concentration, and the smoked cigarette number and the smoking timing reported by the patient, consistency between the report information and the CO concentration measurement value is determined. When the CO concentration measurement value lies between the upper limit value of the CO concentration and the lower limit value of the CO concentration each set based on the smoked cigarette number, the smoking timing and the first and second attenuation functions of the CO concentration, the report information and the CO concentration measurement value are determined to be consistent with each other. On the other hand, when the CO concentration measurement value is greater than the upper limit value of the CO concentration, the report information is determined as underreporting, and, when the CO concentration measurement value is equal to or less than the lower limit value of the CO concentration, the report information is determined as overreporting.

As one example, in the case where the report information from the patient indicates that the patient smoked 5 cigarettes 6 hours before, the upper limit value of the CO concentration and the lower limit value of the CO concentration are, respectively, 49.0 ppm and 28.5 ppm, based on the first and second attenuation functions of the CO concentration. When the CO concentration measurement value is 35.0 ppm, and is compared with the upper limit value of the CO concentration being 49.0 ppm and the lower limit value of the CO concentration being 28.5 ppm, it is evaluated that the CO concentration measurement value is equal to or less than the upper limit value of the CO concentration, and is greater than the lower limit value of the CO concentration. This means that the report information and the CO concentration measurement value are consistent with each other, so that it is determined that the patient smokes 5 cigarettes 6 hours before. Then, based on a result of determination, guidance information for smoking cessation therapy for the patient is generated (S811). A smoking cessation therapy list for use in the third embodiment is presented in Table 3.

TABLE 3

| ID | Report Information | Consistency | Guidance information |
|---|---|---|---|
| 1 | 0 | 1 | "Great! You could keep from smoking today! Please continue the ongoing substitute behavioral therapy (one type of behavioral therapy) based on chewing some gum, to keep up smoking cessation." |
| 2 | >=0 | 2 | "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?" |
| 3 | >4 | 1 | "Considering you have smoked x cigarettes, a fairly large number of nicotinic receptors might already be expressed in brain, and nicotine dependence is considered to be steadily exacerbated. Thus, restart the use of a smoking-cessation aid and keeping a record of the medication (self monitoring: one type of behavioral therapy)" |
| 4 | 1 | 1 | "Unfortunately you have smoked one cigarette. You face a key situation now. Although many persons think that smoking one cigarette is of no matter, it is a terrible error. You should recognize that smoking only one cigarette causes the brain to return to a nicotine-dependent state. Resetting your mind and set starting date of smoking cessation again (declaration of smoking cessation: one type of behavioral therapy)." |
| 5 | 1 | 2 | "In addition to chewing some gum as substitute behavioral therapy (one type of behavioral therapy), ask persons such as your family and friends to support quitting smoking (social support: one type of behavioral therapy)." |
| 6 | 1 | 0 | "Although you restarted smoking, the expression of nicotinic receptors is considered to be not yet so strong. Thus, you can suppress an urge to smoke next one cigarette by discarding cigarettes and an ash tray (environment improving approach: one type of behavioral therapy)." |
| --- | --- | --- | --- |

The numeral presented in "Report Information" in Table 3 denotes smoking cessation therapy corresponding to the smoked cigarette number reported by the patient. That is, the numerals "0" and "1" in "Report Information" mean, respectively, smoking cessation therapies to be performed for: a report that the patient has not smoked; and a report that the patient has smoked one cigarette. Further, the numerals ">=0" and ">4" in "Report Information" mean, respectively, smoking cessation therapies to be performed for any report (i.e., all reports) that the patient has smoked 0 or more cigarettes; and any report that the patient has smoked 4 or more cigarettes. In the third embodiment, the numeral "1" in "Consistency" means that the report information and the CO concentration measurement value are consistent with each other, and the numerals "0" and "2" mean, respectively, that the smoked cigarette number reported by the patient is overreported and inconsistent with the CO concentration measurement value, and that the smoked cigarette number reported by the patient is underreported and inconsistent with the CO concentration measurement value.

As one example, in the case where the report information indicates smoking 5 cigarettes 6 hours before, and the CO concentration measurement value lie between the upper and lower limit values of the CO concentration, it is evaluated that 5 cigarettes were actually smoked as reported by the patient. In this case, from the smoking cessation therapy list presented in Table 3, smoking cessation therapy having the numeral ">4 (the smoked cigarette number is greater than 4) in "Reported Information" and the numeral "1" (consistent) in "Consistency" is selected. "x" included in the guidance information of ID=3 denotes a variable to which the smoked cigarette number indicated by the report information is to be assigned. Thus, in the third embodiment, the server 105 sets x to 5, and generates smoking cessation therapy information for presenting the following guidance information to the patient: "Considering you have smoked 5 cigarettes, a fairly large number of nicotinic receptors might already be expressed in brain, and nicotine dependence is considered to be steadily exacerbated. Thus, restart the use of a smoking-cessation aid and keeping a record of the medication (self monitoring: one type of behavioral therapy)" (S811). In the third embodiment, it becomes possible to perform determination as to whether or not the smoked cigarette number reported by the patient is proper, in addition to the determinations as to the presence or absence of smoking and underreporting. This makes it possible to implement smoking cessation therapy according to the smoked cigarette number. In this example, the patient smoked a fairly large number of cigarettes, specifically, 5 cigarettes. Thus, differently from the case where a small number of cigarettes, such as one cigarette, are smoked, a further advanced smoking cessation therapy is suggested which comprises restarting the use of a smoking-cessation aid.

Further, in the case where the report information indicates that the patient smoked one cigarette 6 hours before, and the CO concentration measurement value is equal to or less than the upper limit value of the CO concentration and greater than the lower limit value of the CO concentration, it is determined that the patient actually smoked one cigarette. In this case, from the smoking cessation therapy list presented in Table 3, smoking cessation therapy having the numeral "1" (smoking of one cigarette) in "Report Information" and the numeral "1" (consistent) in "Consistency" is selected. In this example, ID=4 is selected, and smoking cessation therapy information for presenting the following guidance information to the patient is generated: "Unfortunately you have smoked one cigarette. You face a key situation now. Although many persons think that smoking one cigarette is of no matter, it is a terrible error. You should recognize that smoking only one cigarette causes the brain to return to a nicotine-dependent state. Resetting your mind and set starting date of smoking cessation again (declaration of smoking cessation: one type of behavioral therapy)." (S811).

There are many persons who tentatively smoke one cigarette under erroneous cognition that smoking one cigarette is of no matter. However, in fact, even when a patient smokes only one cigarette, the brain of the patient returns to a previous nicotine-dependent state, and then the patient is likely to return to habitual smoking. In the third embodiment, a result of the determination that the report information indicative of smoking of one cigarette is consistent with the CO concentration measurement value means that the patient smoked only one cigarette and honestly reported this fact. In view of this understanding, it is possible to detect that the patient has cognition that it might be permitted to smoke just one cigarette. In this case, the above guidance information is presented to the patient to correct the erroneous cognition that smoking one cigarette is of no matter, and address quitting smoking again while preventing the patient from smoking next one cigarette (cognitive-behavioral therapy).

On the other hand, in the case where the report information indicates that the patient smoked one cigarette 6 hours before, and the CO concentration measurement value is greater than the upper limit value of the CO concentration, it is determined that the patient reported the presence of smoking of only one cigarette, although he/she actually smoked two or more cigarettes, i.e., underreported. In this case, from the smoking cessation therapy list presented in Table 3, smoking cessation therapy having the numeral "1" (smoking of one cigarette) in "Report Information" and the numeral "2" (inconsistent due to underreporting) in "Consistency" is selected. In this example, ID=5 is selected, and smoking cessation therapy information for presenting the following guidance information to the patient is generated: "In addition to chewing some gum as substitute behavioral therapy (one type of behavioral therapy), ask persons such as your family and friends to support quitting smoking (social support: one type of behavioral therapy)." (S811). In this case, in view of a result of the determination that the report information indicative of smoking is consistent with the CO concentration measurement value means, due to underreporting, the ongoing behavioral therapy is considered to fail to achieve a sufficient effect by itself. Thus, in addition to the substitute behavioral therapy chewing some gum as (one type of behavioral therapy), it is suggested to ask persons such as your family and friends to support quitting smoking (social support: one type of behavioral therapy)."

Further, the underreporting of the smoked cigarette number is made probably because the patient understands smoking during smoking cessation therapy as a negative event. Thus, ID=2 having the numeral ">=0" in "Report Information" and the numeral "2" (underreporting) in "Consistency" is performed to present the following guidance information "Have you ever regretted for and felt discouraged about restarting smoking despite smoking cessation for quite a while? However, please think deeply. Don't you think that even if you restart smoking, it simply causes return to an initial state, and you have nothing to lose, because smoking cessation is originally good for health?", to thereby correct the erroneous negative cognition.

Further, in the case where the report information indicates that the patient smoked two cigarettes 6 hours before, and the CO concentration measurement value is equal to or less than the lower limit value of the CO concentration, it is determined that the patient overreported, because an actually measured CO concentration has only a small value corresponding to smoking of less than two cigarettes. In this case, from the smoking cessation therapy list presented in Table 3, smoking cessation therapy having the numeral "1" (smoking of one cigarette) in "Report Information" and the numeral "0" (inconsistent due to overreporting) in "Consistency" is selected. In this example, ID=6 is selected, and smoking cessation therapy information for presenting the following guidance information to the patient is generated: "Although you restarted smoking, the expression of nicotinic receptors is considered to be not yet so strong. Thus, you can suppress an urge to smoke next one cigarette by discarding cigarettes and an ash tray (environment improving approach: one type of behavioral therapy)." (S811). Specifically, the guidance information is intended to enable the patient to recognize that, although the patient has smoked, an influence of this smoking is lighter than he/she thinks, so as to encourage the patient, and to prevent the patient from restating smoking by implementing the behavioral therapy again based on discarding cigarettes and an ash tray, because the report information indicative of the presence of smoking also suggests that the patient still have cigarettes and an ash tray.

Further, as with the second embodiment, as a substitute for the CO concentration, the concentration of cotinine contained in saliva of the patient may also be used as the biomarker of the patient to implement the embodiments of the present invention. For example, in addition to the upper limit value of the cotinine concentration described in connection with the second embodiment, a lower limit value of the CO concentration can be set based on an attenuation function of the cotinine concentration obtained when the half-life of the cotinine concentration C is set to 15 hours.

Figure 14:
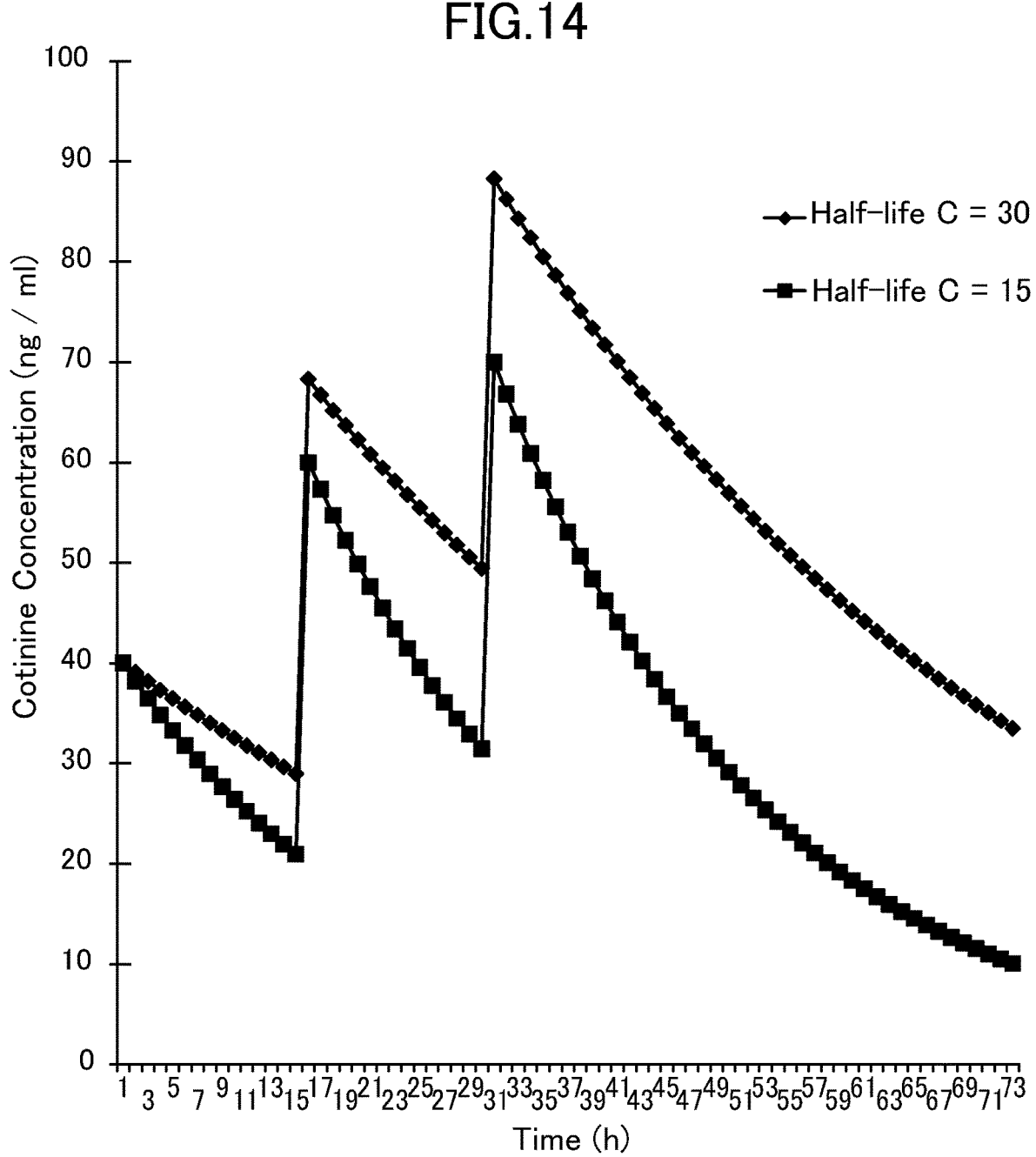
FIG. 14 is a graph presenting an attenuation function of the nicotine concentration in the system according to the third embodiment.

In the case where smoking is performed at intervals of a certain time, as regards the lower limit value of the cotinine concentration, a cotinine concentration value at an elapsed time T from an initial smoking can be estimated using the formula (7) in which the half-life is set to 15 hours, and a cotinine concentration value since then can be estimated using the formula (6) in which the half-life is set to 15 hours, so as to calculate a second attenuation function of the CO concentration, as with the upper limit value of the cotinine concentration. As one example, FIG. 14 depicts attenuation curves of the cotinine concentration values for the upper and lower limit values of the CO concentration, in the case where 2 cigarettes are smoked, respectively, after 15 hours and after 48 hours from initial smoking (0 hour).

The above embodiments have been described based on an example where the patient-side device 103 and the biomarker concentration meter 104 are formed as separate components. Alternatively, the embodiments of the present invention can also be performed using a unit obtained by integrating the two components together. Further, the patient-side device 103 such as a smartphone may be configured such that it performs the consistency determination (S810), and then transmits a result of the consistency determination to the server 102, and the server 102 may be configured to generate the smoking cessation therapy information based on the result of the consistency determination (S811). Further, the patient-side device 103 may be configured to perform the consistency determination (S810) and generation of the smoking cessation therapy information (S811). Further, the system according to each of the above embodiments may comprise a plurality of computers configured to execute all steps in the embodiments of the present invention, in their entireties.

Although the present invention has been described by way of the above embodiments in order to express the present invention, it should be noted that the present invention is not limited to such embodiments in any way. It is obvious to a person of ordinary skill in the art that the present invention may be implemented in various forms or configurations without departing from the spirit and scope thereof as set forth in appended claims.

LIST OF REFERENCE SIGNS

100: system
101: network
102: server
103: patient-side device
104: CO monitor
104: biomarker concentration meter
201: processing unit
202: display unit
203: input unit
204: storage unit
205: communication unit
206: server program
210: bus
301: processing unit
302: display unit
303: input unit
303: patient-side device
304: storage unit
305: communication unit
306: patient program
310: bus
401: processing unit
402: display unit
403: input unit
404: storage unit
405: communication unit
406: meter program
407: sensor
410: bus
501: control section
502: display section
503: input section
504: storage section
505: communication section
601: control section
602: display section
603: input section
604: storage section
605: communication section
701: control section
702: display section
703: input section
704: storage section
705: communication section
707: sensor

The invention claimed is:

1. A non-transitory computer-readable medium with instructions stored thereon, that when executed by a processor, perform the steps comprising:
   prompting a patient-side device to display:
      a message that requests a patient to input report information indicating whether the patient has smoked; and
      a message that requests the patient to provide a biological sample to a biomarker concentration meter that measures a biomarker concentration indicating an actual smoking state of the patient;
   receiving, from the patient-side device, the report information input by the patient;
   receiving, from the biomarker concentration meter, a biomarker concentration measurement value measured from the biological sample by the biomarker concentration meter;
   comparing the biomarker concentration measurement value with a biomarker concentration reference value to determine consistency between the biomarker concentration measurement value and the report information for determining whether the report information input by the patient is false;
   based on a result of the consistency determination and the actual smoking state of the patient, generating smoking cessation therapy information for smoking cessation therapy to be performed for the patient; and
   transmitting the smoking cessation therapy information to the patient-side device that presents information for the smoking cessation therapy to the patient based on the smoking cessation therapy information.

2. The non-transitory computer-readable medium according to claim 1, wherein
the instructions cause the computer to further execute receiving a time stamp that indicates a clock time of the measurement of the biomarker concentration measurement value, and
the measurement clock time is determined by the biomarker concentration meter or by a device for transmitting the biomarker concentration measurement value.

3. The non-transitory computer-readable medium according to claim 1, wherein
the report information includes a number of cigarettes smoked and a smoking timing, and
the determining of the consistency includes:
based on the number of cigarettes smoked, the smoking timing and an attenuation function of the biomarker concentration, setting an upper limit value of the biomarker concentration, as the biomarker concentration reference value;
comparing the biomarker concentration measurement value with the upper limit value of the biomarker concentration; and
when the biomarker concentration measurement value is greater than the upper limit value of the biomarker concentration, determining that the report information and the biomarker concentration measurement value are inconsistent with each other.

4. The non-transitory computer-readable medium according to claim 3, wherein the determining of the consistency further includes:
based on the number of cigarettes smoked, the smoking timing, and the attenuation function of the biomarker concentration, setting a lower limit value of the biomarker concentration, as the biomarker concentration reference value;
comparing the biomarker concentration measurement value with the lower limit value of the biomarker concentration;
when the biomarker concentration measurement value is greater than the upper limit value of the biomarker concentration, determining that the biomarker concentration measurement value and the report information are inconsistent with each other, due to underreporting; and
when the biomarker concentration measurement value is equal to or greater than the lower limit value of the biomarker concentration, determining that the biomarker concentration measurement value and the report information are inconsistent with each other, due to overreporting.

5. The non-transitory computer-readable medium according to claim 1, wherein the biological sample is exhaled breath, and a biomarker is carbon monoxide (CO), and the biomarker concentration meter is a CO concentration meter.

6. The non-transitory computer-readable medium according to claim 1, wherein the biological sample is saliva, and a biomarker is nicotine, and the biomarker concentration meter is a nicotine concentration meter.

7. The non-transitory computer-readable medium according to claim 1, wherein
in the determining of the consistency, the processor determines whether both of the biomarker concentration measurement value and the report information indicate that the patient has not smoked.

8. The non-transitory computer-readable medium according to claim 1, wherein
in the generating of the smoking cessation therapy information, the processor determines the smoking cessation therapy information based on whether at least one of the biomarker concentration measurement value and the report information indicate that the patient has smoked.

9. A system comprising a computer used for a patient who is attempting to quit smoking, wherein the computer execute:
prompting, by the computer, a patient-side device to display;
a message that requests a patient to input report information indicating whether the patient has smoked; and
a message that requests the patient to provide a biological sample to a biomarker concentration meter that measures a biomarker concentration indicating a smoking state of the patient;
receiving, by the computer from the patient-side device, the report information input by the patient;
receiving, from the biomarker concentration meter, a biomarker concentration measurement value measured from the biological sample;
comparing, by the computer, the biomarker concentration measurement value with a biomarker concentration reference value to determine consistency between the biomarker concentration measurement value and the report information for determining whether the report information input by the patient is false;
based on a result of the consistency determination and the actual smoking state of the patient, generating, by the computer, smoking cessation therapy information for smoking cessation therapy to be performed for the patient; and
based on the smoking cessation therapy information, presenting, by the patient-side device to the patient, information for the smoking cessation therapy.

10. A method performed with a computer used for a patient who is attempting to quit smoking, the method comprising:
prompting, by the computer, a patient-side device to display:
a message that requests a patient to input report information indicating whether the patient has smoked; and
a message that requests the patient to provide a biological sample to a biomarker concentration meter that measures a biomarker concentration indicating a smoking state of the patient;
receiving, by the computer from the patient-side device, the report information input by the patient;
measuring receiving, by the computer from the biomarker concentration meter, a biomarker concentration measurement value measured from the biological sample;
comparing, by the computer, the biomarker concentration measurement value with a biomarker concentration reference value to determine consistency between the biomarker concentration measurement value and the report information for determining whether the report information input by the patient is false; and
based on a result of the consistency determination and the actual smoking state of the patient, generating, by the computer, smoking cessation therapy information for smoking cessation therapy to be performed for the patient.

\* \* \* \* \*